(12) United States Patent
Jakobsen et al.

(10) Patent No.: US 10,682,469 B2
(45) Date of Patent: Jun. 16, 2020

(54) DRUG DELIVERY SYSTEM WITH MAGNETIC RING AND SENSORS ARRANGED IN A RING PATTERN

(71) Applicant: Novo Nordisk A/S, Bagsvaerd (DK)

(72) Inventors: Nikolaj Eusebius Jakobsen, Soeborg (DK); Preben Mikael Nielsen, Holbaek (DK); Nikolaj Frogner Krusell, Risskov (DK); Laurits Hoejgaard Olesen, Kobenhavn K (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 16/732,443

(22) Filed: Jan. 2, 2020

(65) Prior Publication Data

US 2020/0147317 A1 May 14, 2020

Related U.S. Application Data

(63) Continuation of application No. PCT/EP2018/083324, filed on Dec. 3, 2018.

(30) Foreign Application Priority Data

Dec. 4, 2017 (EP) .................................. 17205062
Dec. 4, 2017 (EP) .................................. 17205063

(51) Int. Cl.
*A61M 5/00* (2006.01)
*A61M 5/315* (2006.01)

(52) U.S. Cl.
CPC ...... *A61M 5/31553* (2013.01); *A61M 5/3158* (2013.01); *A61M 5/31525* (2013.01); *A61M 5/31556* (2013.01); *A61M 2205/3317* (2013.01)

(58) Field of Classification Search
CPC .......... A61M 5/31553; A61M 5/31545; A61M 5/31568; A61M 5/31551; A61M 5/31535; A61M 5/20
See application file for complete search history.

(56) References Cited

U.S. PATENT DOCUMENTS

| 6,585,698 | B1 | 7/2003 | Packman et al. |
| 7,511,480 | B2 * | 3/2009 | Steffen ............. A61M 5/31525 324/207.23 |

(Continued)

FOREIGN PATENT DOCUMENTS

| DE | 102009003721 A1 | 10/2010 |
| DK | 200100240 | 11/2001 |

(Continued)

OTHER PUBLICATIONS

ATMEL Datasheet ATtiny 26, 2010, pp. 1-182.
(Continued)

*Primary Examiner* — Rebecca E Eisenberg
(74) *Attorney, Agent, or Firm* — Wesley Nicolas

(57) ABSTRACT

A drug delivery system comprises an indicator element and a sensor system. The indicator element is arranged to rotate relative to a reference component and corresponding to a reference axis and comprises a magnetic ring. The sensor system comprises a plurality of magnetometers arranged non-rotational relative to the reference component and adapted to determine continuous magnetic field values from the plurality of dipole magnets, as well as processor means configured to determine on the basis of measured values from the plurality of magnetometers a rotational position and/or a rotational movement of the indicator element.

14 Claims, 15 Drawing Sheets

(56) References Cited

U.S. PATENT DOCUMENTS

| | | | |
|---|---|---|---|
| 8,771,233 B2 | 7/2014 | Watanabe et al. | |
| 8,882,704 B2* | 11/2014 | Fago | A61M 5/31525 604/67 |
| 9,022,988 B1* | 5/2015 | Shaban | A61M 5/315 604/189 |
| 2002/0101210 A1 | 8/2002 | Boisvert et al. | |
| 2006/0175427 A1 | 8/2006 | Jonientz et al. | |
| 2009/0318865 A1 | 12/2009 | Moller et al. | |
| 2013/0079727 A1* | 3/2013 | Schildt | A61M 5/31525 604/207 |
| 2014/0243787 A1* | 8/2014 | Mukai | A61M 5/20 604/506 |
| 2014/0276583 A1 | 9/2014 | Chen et al. | |
| 2015/0352288 A1 | 12/2015 | Andersen | |
| 2016/0030679 A1* | 2/2016 | Nielsen | A61M 5/20 604/189 |
| 2017/0286638 A1* | 10/2017 | Searle | A61M 5/16804 |
| 2018/0200452 A1* | 7/2018 | Marcoz | G01R 33/0206 |
| 2018/0207366 A1* | 7/2018 | Marcoz | A61M 5/31533 |
| 2020/0023137 A1* | 1/2020 | Byerly | A61M 5/31551 |

FOREIGN PATENT DOCUMENTS

| | | |
|---|---|---|
| EP | 1808193 A1 | 7/2007 |
| EP | 2060284 A1 | 5/2009 |
| GB | 2256050 A | 11/1992 |
| JP | 2013228313 A | 11/2013 |
| WO | 9709080 A1 | 3/1997 |
| WO | 02064196 | 8/2002 |
| WO | 03/047426 | 6/2003 |
| WO | 04078241 | 9/2004 |
| WO | 2005009231 A1 | 2/2005 |
| WO | 2005/046559 A2 | 5/2005 |
| WO | 05/110387 A2 | 11/2005 |
| WO | 06/045525 | 5/2006 |
| WO | 2009062675 A1 | 5/2009 |
| WO | 2010005688 A2 | 1/2010 |
| WO | 2010052275 A2 | 5/2010 |
| WO | 2010070799 A1 | 6/2010 |
| WO | 2010/098927 A1 | 9/2010 |
| WO | 2010/098928 A1 | 9/2010 |
| WO | 2010/098929 A1 | 9/2010 |
| WO | 2010/098931 A1 | 9/2010 |
| WO | 2010112575 A1 | 10/2010 |
| WO | 2010/128493 A2 | 11/2010 |
| WO | 2010/142598 A2 | 12/2010 |
| WO | 2013050535 A2 | 4/2013 |
| WO | 2014/020008 A1 | 2/2014 |
| WO | 2014037331 A1 | 3/2014 |
| WO | 2014161952 A1 | 10/2014 |
| WO | 2016050902 A1 | 4/2016 |
| WO | 2016142216 A1 | 9/2016 |
| WO | 2017013463 A1 | 1/2017 |

OTHER PUBLICATIONS

U.S. Appl. No. 13/375,033—Advisory Action dated Jun. 29, 2015.
U.S. Appl. No. 13/375,033—Office Action dated Nov. 7, 2014.
WO2010142598—International Preliminary Report on Patentability, dated Dec. 6, 2011.

\* cited by examiner

DRUG DELIVERY SYSTEM WITH MAGNETIC RING AND SENSORS ARRANGED IN A RING PATTERN

REFERENCE TO RELATED APPLICATIONS

This application is a continuation of International Application PCT/EP2018/083324 (published as WO 2019/110494), filed Dec. 3, 2018, which claimed priority of European Patent Applications 17205062.7, filed Dec. 4, 2017; and 17205063.5, filed Dec. 4, 2017; the contents of all above-named applications are incorporated herein by reference.

The present invention generally relates to medical systems and devices for which the generation, collecting and storing of data are relevant. In specific embodiments the invention relates to systems and devices for capturing and organizing drug delivery dose data in a reliable and user-friendly way.

BACKGROUND OF THE INVENTION

In the disclosure of the present invention reference is mostly made to drug delivery devices comprising a threaded piston rod driven by a rotating drive member, such devices being used e.g. in the treatment of diabetes by delivery of insulin, however, this is only an exemplary use of the present invention.

Drug Injection devices have greatly improved the lives of patients who must self-administer drugs and biological agents. Drug Injection devices may take many forms, including simple disposable devices that are little more than an ampoule with an injection means or they may be durable devices adapted to be used with prefilled cartridges. Regardless of their form and type, they have proven to be great aids in assisting patients to self-administer injectable drugs and biological agents. They also greatly assist care givers in administering injectable medicines to those incapable of performing self-injections.

A general type of drug delivery devices suitable for delivery of a user set amount of drug comprises a spring which is strained during dose setting, the stored energy subsequently being used to expel the set dose of drug from a cartridge arranged in the device, this providing what can be termed an automatic drug delivery device in contrast to a traditional manual drug delivery device in which the set dose of drug is expelled by the user applying an axial force to a proximally extending push button. The user usually strains a spring by rotating a rotatable dose setting member, the force thereby applied by the user being stored in the spring for later release.

Performing the necessary insulin injection at the right time and in the right size is essential for managing diabetes, i.e. compliance with the specified insulin regimen is important. In order to make it possible for medical personnel to determine the effectiveness of a prescribed dosage pattern, diabetes patients are encouraged to keep a log of the size and time of each injection. However, such logs are normally kept in handwritten notebooks, and the logged information may not be easily uploaded to a computer for data processing. Furthermore, as only events, which are noted by the patient, are logged, the note book system requires that the patient remembers to log each injection, if the logged information is to have any value in the treatment of the patient's disease. A missing or erroneous record in the log results in a misleading picture of the injection history and thus a misleading basis for the medical personnel's decision making with respect to future medication. Accordingly, it may be desirable to automate the logging of injection information from medication delivery systems.

Though some injection devices integrate this monitoring/acquisition mechanism into the device itself, e.g. as disclosed in US 2009/0318865 and WO 2010/052275, most devices of today are without it. The most widely used devices are purely mechanical devices being either durable or prefilled. The latter devices are to be discarded after being emptied and so inexpensive that it is not cost-effective to build-in electronic data acquisition functionality in the device it-self. Addressing this problem a number of solutions have been proposed which would help a user to generate, collect and distribute data indicative of the use of a given medical device.

For example, WO 2014/037331 describes in a first embodiment an electronic supplementary device (also named "add-on module" or "add-on device") adapted to be releasably attached to a drug delivery device of the pen type. The device includes a camera and is configured to perform optical character recognition (OCR) on captured images from a rotating scale drum visible through a dosage window on the drug delivery device, thereby to determine a dose of medicament that has been dialed into the drug delivery device. WO 2014/037331 also describes a second embodiment of an electronic supplementary device adapted to be releasably attached to a drug delivery device of the pen type comprising a drive screw extending proximally from the device corresponding to a set dose. The supplementary device comprises sensor means for determining axial extension of the drive screw as well as sensor means for detecting operation of the proximal delivery button. WO 2014/020008 discloses an electronic supplementary device adapted to be releasably attached to a drug delivery device of the pen type. The device includes a camera and is configured to determine scale drum values based on OCR. To properly determine the size of an expelled dose the supplementary device further comprises additional electromechanical sensor means to determine whether a dose size is set, corrected or delivered. A further external device for a pen device is shown in WO 2014/161952.

WO 2017/013463 discloses an add-on dose control system to be used in combination with a pen-formed drug delivery device, the dose control system being adapted to be mounted on the drug delivery device and comprising a magnetic component adapted to rotate during use of the drug delivery device, as well as magnetic detection means adapted to process information from the magnetic component in order to determine a set or expelled dose amount of drug.

US 2006/0175427 discloses a pen-formed drug delivery device provided with a position sensor comprising a magnetic ring coupled to a setting element and a number of magnetic switches allowing an angular position of the magnetic ring to be determined. In an exemplary embodiment a rotation of 45 degrees can be detected.

US 2015/0352288 discloses a medical injection system with dose capturing means in the form of a magnetic linear encoder comprising a multi-pole magnetic ring and a magnetic sensor in the form of a Hall element.

Having regard to the above, it is an object of the present invention to provide systems, devices and methods allowing secure, easy and efficient operation of a drug delivery system, of the automatic type comprising an indicator element and a sensor system adapted for capturing of dose related data. The system may be in the form of an assembly comprising a drug delivery device and an add-on device adapted to be releasably mounted on the drug delivery device.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in a first aspect of the invention a drug delivery system is provided. The system comprises a housing forming a reference component, a drug reservoir or means for receiving a drug reservoir, drug expelling means comprising a rotatable dose setting member allowing a user to set a dose amount of drug to be expelled, a release member actuatable between a proximal position and a distal position, the proximal position allowing a dose amount to be set, the distal position allowing the drug expelling means to expel a set dose, a drive spring arranged to be strained during dose setting and released by the release member to thereby drive expelling of an amount of drug from the drug reservoir, the drive spring being formed from a magnetisable material, and an indicator element comprising a plurality of dipole magnets and being adapted to rotate relative to the reference component and corresponding to a reference axis during setting and/or expelling of a dose amount, the amount of rotation being indicative of the size of the set and/or expelled dose amount. The drug delivery system further comprises a sensor system comprising a plurality of magnetometers arranged non-rotational relative to the reference component and adapted to determine continuous magnetic field values from the plurality of dipole magnets (i.e. in response to continuously varying magnetic field values within a specified operational range as input, the magnetometers produce a corresponding continuously varying output measurement), and processor means configured to determine on the basis of measured values from the plurality of magnetometers a rotational position and/or a rotational movement of the indicator element, wherein the determined rotational position and/or a rotational movement of the indicator element correspond to the set and/or expelled dose amount.

By this arrangement a drug delivery system is provided in which external as well as internal magnetic disturbances can be cancelled out to a large extent in a cost-effective and energy-effective way by signal processing algorithms based on input from the rotating plurality of dipole magnets.

In exemplary embodiments the indicator element comprises two, three or four dipole magnets, e.g. two dipole magnets forming a quadrupole indicator element, with the processor means being configured to determine on the basis of measured values from the plurality of magnetometers a rotational position of the indicator element with a resolution of at least 18 degrees corresponding to 20 increments for a rotational dose setting mechanism, or of at least 15 degrees corresponding to 24 increments for a rotational dose setting mechanism.

The indicator element may be ring-formed and arranged transversely to the reference axis, and the poles of the dipole magnets may be arranged circumferentially equidistantly. The indicator element may be formed fully or partly of a polymeric material containing magnetic particles, the polymeric material having been magnetized to provide the plurality of dipole magnets.

The drive spring may be in the form of a helical metal torque spring in which the coil may be open or fully or partly closed.

In an exemplary embodiment and relative to the reference axis, the plurality of magnetometers is arranged in a proximal position, the drive spring is arranged in a distal position, and the indicator element is arranged in an intermediate position.

At least a portion of the magnetometers may be adapted to measure a magnetic field in the axial as well as a tangential direction. Alternatively, the magnetometers may be in the form of 3-axis "compass" sensors adapted to measure a magnetic field in the axial, tangential as well as radial direction. The processor means may be configured to determine a rotational position and/or a rotational movement of the indicator element on the basis of measured values from the plurality of magnetometers in the axial and in tangential directions only, i.e. the ability to measure a magnetic field in the radial direction is not utilized, this lowering energy consumption and reducing the signal processing requirements. This concept is based on the realization that in a typical drug delivery device the largest degree of slack for a rotating indicator member is based on tolerances in the radial direction.

In an exemplary embodiment the difference between phase angle from tangential and axial signals can be used as a quality indicator. When for a given exemplary embodiment a difference up to a first threshold can be expected due to tolerances on the mechanical and electrical system, then if the difference exceeds a second threshold it can be taken as a sign that there is a large disturbance and the measurement is unreliable, this resulting in an error condition being indicated to the user.

The rotational position and/or a rotational movement of the indicator element may be determined using a DFT algorithm.

In an exemplary embodiment the drug delivery system comprises a metallic shield structure circumferentially encasing the plurality of magnetometers, the indicator element, and at least a proximal portion of the magnetisable drive spring. In a specific embodiment the circumscribing diameter for the magnetisable drive spring is larger than the circumscribing diameter for the indicator element.

In a specific embodiment the above described drug delivery system is in the form of an assembly comprising a drug delivery device and an add-on device adapted to be releasably mounted on the drug delivery device, the drug delivery device comprising the housing, the drug reservoir or the means for receiving a drug reservoir, the drug expelling means, the release member, the drive spring, and the indicator element. The add-on device comprises the plurality of magnetometers and the processor means.

In a further aspect of the invention an add-on device adapted to be releasably mounted on a drug delivery device is provided. The drug delivery device comprises a housing forming a reference component, a drug reservoir or means for receiving a drug reservoir, drug expelling means comprising a rotatable dose setting member allowing a user to set a dose amount of drug to be expelled, a release member actuatable between a proximal position and a distal position, the proximal position allowing a dose amount to be set, the distal position allowing the drug expelling means to expel a set dose, a drive spring arranged to be strained during dose setting and released by the release member to thereby drive expelling of an amount of drug from the drug reservoir, the drive spring being formed from a magnetisable material, and an indicator element comprising a plurality of dipole magnets and being adapted to rotate relative to the reference component and corresponding to a reference axis during setting and/or expelling of a dose amount, the amount of rotation being indicative of the size of the set and/or expelled dose amount. The add-on device comprises a plurality of magnetometers arranged non-rotational relative to the reference component and adapted to determine continuous magnetic field values from the plurality of dipole magnets, and processor means configured to determine on the basis of measured values from the plurality of magnetometers a rotational position and/or a rotational movement of the indicator element, wherein the determined rotational position and/or a rotational movement of the indicator element correspond to a set and/or expelled dose amount.

The number of dipole magnets in the drug delivery device may be 2, 3 or 4, and the processor means may be configured to determine on the basis of measured values from the plurality of magnetometers a rotational position of the indicator element with a resolution of at least 18 degrees or at least 15 degrees. The processor means may be configured to determine a rotational position and/or a rotational movement of the indicator element on the basis of measured values from the plurality of magnetometers in the axial and in tangential directions only. The add-on device may be additionally be modified as described above for the system.

In a further aspect of the invention a drug delivery device adapted to be used in combination with an add-on device adapted to be releasably mounted thereon is provided. The drug delivery device comprises a housing forming a reference component, a drug reservoir or means for receiving a drug reservoir, drug expelling means comprising a rotatable dose setting member allowing a user to set a dose amount of drug to be expelled, a release member actuatable between a proximal position and a distal position, the proximal position allowing a dose amount to be set, the distal position allowing the drug expelling means to expel a set dose, a drive spring arranged to be strained during dose setting and released by the release member to thereby drive expelling of an amount of drug from the drug reservoir, the drive spring being formed from a magnetisable material, and an indicator element comprising a plurality of dipole magnets and being adapted to rotate relative to the reference component (101, 601) and corresponding to a reference axis during setting and/or expelling of a dose amount, the amount of rotation being indicative of the size of the set and/or expelled dose amount.

The number of dipole magnets may be two, three or four. The indicator element may be ring-formed and arranged transversely to the reference axis.

In an exemplary embodiment, relative to the reference axis, the drive spring is arranged in a distal position and the indicator element is arranged in a proximal position.

In a yet further aspect of the invention a sensor assembly is provided comprising a magnetic indicator element and a sensor system, wherein the magnetic indicator element is arranged to rotate relative to a reference component and corresponding to a reference axis. The sensor system comprises a plurality of magnetometers arranged non-rotational relative to the reference component and adapted to determine magnetic field values from the magnetic indicator element, and processor means configured to determine on the basis of measured values from the plurality of magnetometers a rotational position and/or a rotational movement of the magnetic indicator element. The sensor assembly further comprises a magnetisable metal component. The plurality of magnetometers is, relative to the reference axis, arranged in a proximal position, the magnetisable metal component is arranged in a distal position, and the magnetic indicator element is arranged in an intermediate position. The sensor assembly further comprises a metallic shield structure circumferentially encasing the plurality of magnetometers, the magnetic indicator element, and at least a proximal portion of the magnetisable metal component.

By this arrangement a sensor assembly is provided with a shield which does not only shield the sensor system from external magnetic fields, but also helps divert any unintended internal magnetic field introduced by the magnetisable metal component when magnetized. By reducing the strength of the disturbing field from the metal component it may enable the use of fewer sensors and thus lower signal processing requirements to obtain required accuracy and redundancy, and thereby reduce both costs and power consumption.

The circumscribing diameter for the magnetisable metal component may be larger than the circumscribing diameter for the magnetic indicator element. In this way the shield will to a higher degree be able to absorb magnetic lines from a magnetized member than the magnetic indicator element.

In an exemplary embodiment the magnetisable metal component is in the form of a helical metal spring. The magnetic indicator element may be ring-formed and may comprise a plurality of dipole magnets which may be arranged circumferentially equidistantly.

The rotational position and/or a rotational movement of the magnetic indicator element is/are determined using a DFT algorithm.

The metallic shield structure may at least in part be manufactured from mu-metal. In an exemplary embodiment the metallic shield structure comprises an outer circumferential shield member formed from a first metallic material optimized for shielding from external magnetic fields, and an inner circumferential shield member formed from a second metallic material optimized for diverting and guiding inner magnetic fields, e.g. mu-metal.

The magnetic indicator element may be formed fully or partly of a polymeric material containing magnetic particles, the polymeric material having been magnetized to provide the magnetic indicator element or the plurality of dipole magnets. The magnetometers may be 3D compass sensors.

In a further aspect of the invention an add-on device adapted to be releasably mounted on a drug delivery device is provided. The drug delivery device comprises a housing having a generally cylindrical proximal portion to which is mounted a rotatable dose setting member allowing a user to set a dose amount of drug to be expelled. The device further comprises a drug reservoir or means for receiving a drug reservoir, an expelling mechanism adapted to expel a user-set amount of drug from a contained cartridge, and a magnetic indicator element adapted to rotate relative to the housing during dose setting and/or expelling of a dose amount, the amount of movement being indicative of the size of the set and/or expelled dose amount. The add-on device comprises a housing comprising a proximal portion and a distal generally cylindrical coupling portion adapted to receive the proximal portion of the drug delivery device with the rotatable dose setting member, and a sensor system arranged in the proximal portion. The sensor system comprises a plurality of magnetometers, and processor means configured to determine, when the add-on device is mounted on a drug delivery device, on the basis of measured values from the plurality of magnetometers a rotational position and/or a rotational movement of an indicator element. The add-on device further comprises a metallic shield structure circumferentially encasing the plurality of magnetometers and extending distally and circumferentially into the coupling portion, the latter allowing the shield to help divert magnetic fields introduced by a magnetisable metal component comprised in given drug delivery device proximal portion to which the add-on device is attached.

The metallic shield structure may be at least in part manufactured from mu-metal. The shield structure may comprise an outer circumferential shield member formed from a first metallic material optimized for shielding from external magnetic fields, e.g. from steel, and an inner circumferential shield member formed from a second metallic material optimized for diverting and guiding inner magnetic fields, e.g. at least in part formed from mu-metal.

As used herein, the term "insulin" is meant to encompass any drug-containing flowable medicine capable of being passed through a delivery means such as a cannula or hollow needle in a controlled manner, such as a liquid, solution, gel or fine suspension, and which has a blood glucose controlling effect, e.g. human insulin and analogues thereof as well as non-insulins such as GLP-1 and analogues thereof. In the description of exemplary embodiments reference will be made to the use of insulin, however, the described module could also be used to create logs for other types of drug, e.g. growth hormone.

BRIEF DESCRIPTION OF THE DRAWINGS

In the following embodiments of the invention will be described with reference to the drawings, wherein.

In the figures like structures are mainly identified by like reference numerals.

DESCRIPTION OF EXEMPLARY EMBODIMENTS

When in the following terms such as "upper" and "lower", "right" and "left", "horizontal" and "vertical" or similar relative expressions are used, these only refer to the appended figures and not necessarily to an actual situation of use. The shown figures are schematic representations for which reason the configuration of the different structures as well as their relative dimensions are intended to serve illustrative purposes only. When the term member or element is used for a given component it generally indicates that in the described embodiment the component is a unitary component, however, the same member or element may alternatively comprise a number of sub-components just as two or more of the described components could be provided as unitary components, e.g. manufactured as a single injection moulded part. The term "assembly" does not imply that the described components necessarily can be assembled to provide a unitary or functional assembly during a given assembly procedure but is merely used to describe components grouped together as being functionally more closely related.

Figure 1A:
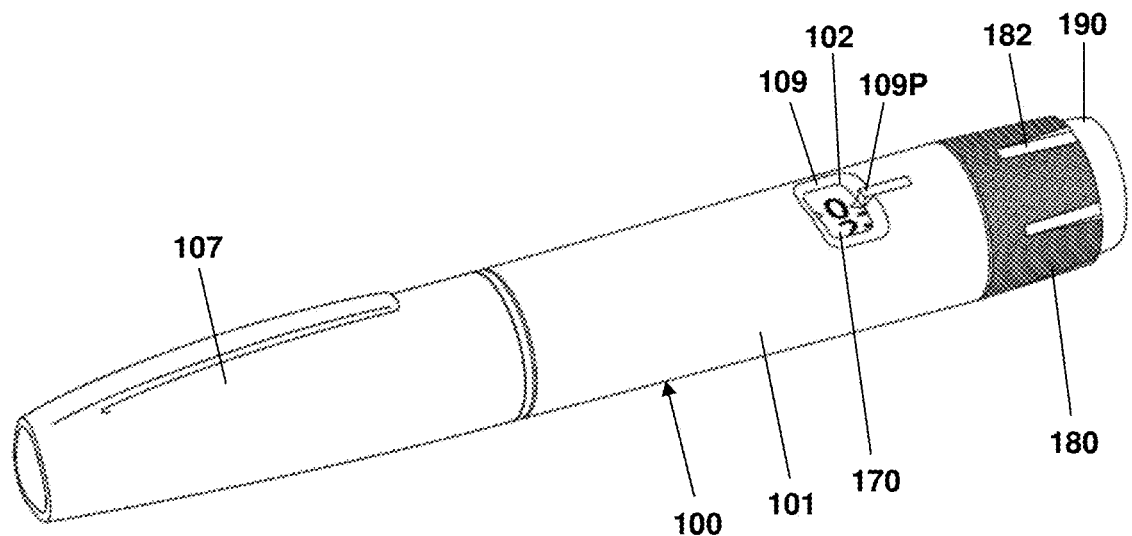
FIG. 1A shows a pen device.

Before turning to embodiments of the present invention per se, an example of a prefilled drug delivery will be described, such a device providing the basis for the exemplary embodiments of the present invention. Although the pen-formed drug delivery device 100 shown in FIGS. 1-3 may represent a "generic" drug delivery device, the actually shown device is a FlexTouch® prefilled drug delivery pen as manufactured and sold by Novo Nordisk A/S, Bagsværd, Denmark.

The pen device 100 comprises a cap part 107 and a main part having a proximal body or drive assembly portion with a housing 101 in which a drug expelling mechanism is arranged or integrated, and a distal cartridge holder portion in which a drug-filled transparent cartridge 113 with a distal needle-penetrable septum is arranged and retained in place by a non-removable cartridge holder attached to the proximal portion, the cartridge holder having openings allowing a portion of the cartridge to be inspected as well as distal coupling means 115 allowing a needle assembly to be releasably mounted. The cartridge is provided with a piston driven by a piston rod forming part of the expelling mechanism and may for example contain an insulin, GLP-1 or growth hormone formulation. A proximal-most rotatable dose setting member 180 with a number of axially oriented grooves 182 serves to manually set a desired dose of drug shown in display window 102 and which can then be expelled when the button 190 is actuated. The window is in the form of an opening in the housing surrounded by a chamfered edge portion 109 and a dose pointer 109P, the window allowing a portion of a helically rotatable indicator member 170 (scale drum) to be observed. Depending on the type of expelling mechanism embodied in the drug delivery device, the expelling mechanism may comprise a spring as in the shown embodiment which is strained during dose setting and then released to drive the piston rod when the release button is actuated. Alternatively the expelling mechanism may be fully manual in which case the dose member and the actuation button moves proximally during dose setting corresponding to the set dose size, and then is moved distally by the user to expel the set dose, e.g. as in a FlexPen® manufactured and sold by Novo Nordisk A/S.

Figure 1B:
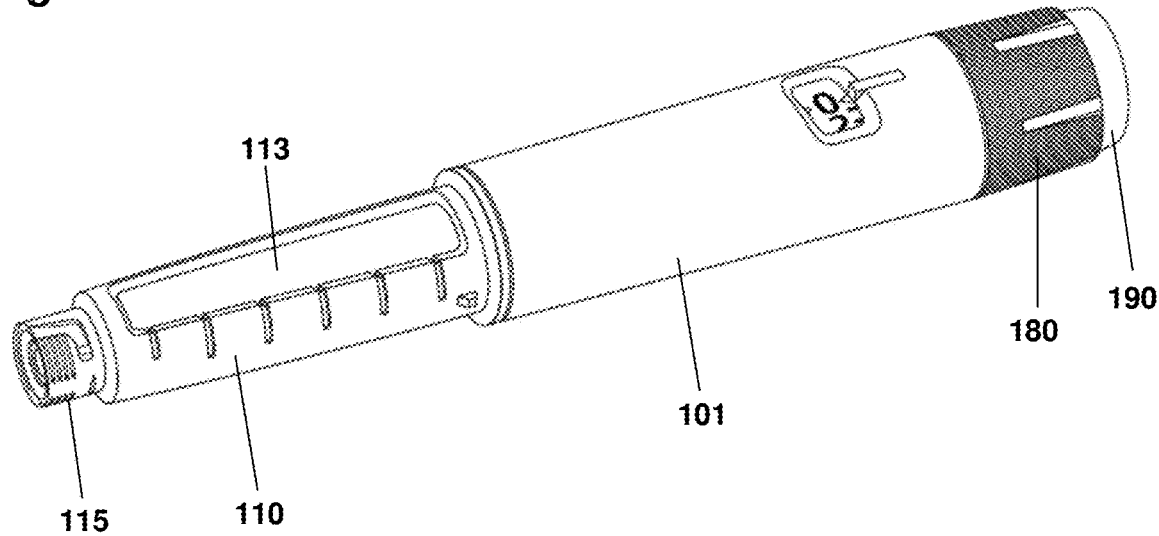
FIG. 1B shows the pen device of FIG. 1A with the pen cap removed.

Although FIG. 1 shows a drug delivery device of the prefilled type, i.e. it is supplied with a pre-mounted cartridge and is to be discarded when the cartridge has been emptied, in alternative embodiments the drug delivery device may be designed to allow a loaded cartridge to be replaced, e.g. in the form of a "rear-loaded" drug delivery device in which the cartridge holder is adapted to be removed from the device main portion, or alternatively in the form of a "front-loaded" device in which a cartridge is inserted through a distal opening in the cartridge holder which is non-removable attached to the main part of the device.

As the invention relates to electronic circuitry adapted to interact with a drug delivery device, an exemplary embodiment of such a device will be described for better understanding of the invention.

Figure 2:
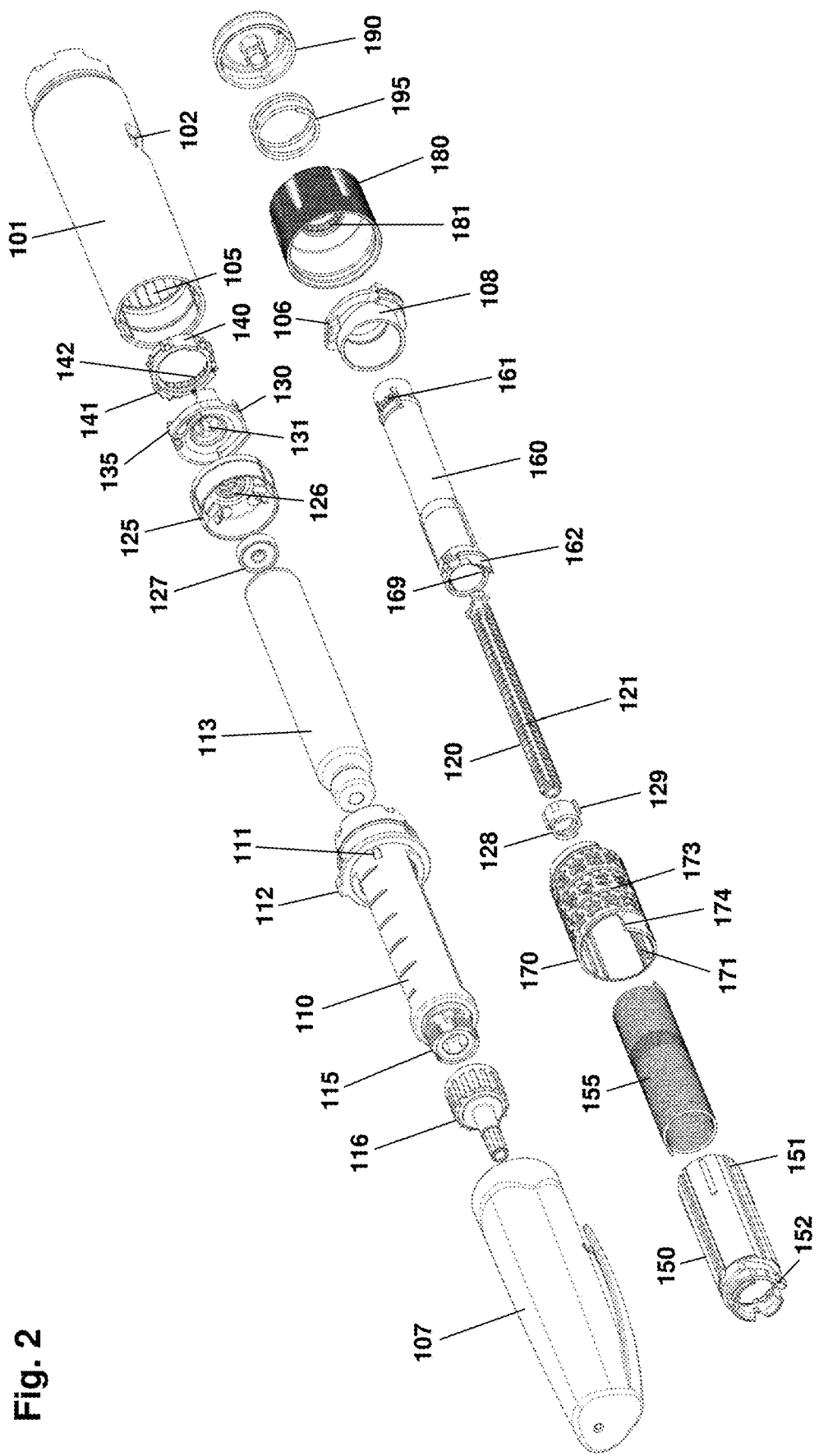
FIG. 2 shows in an exploded view the components of the pen device of FIG. 1A, FIGS. 3A and 3B show in sectional views an expelling mechanism in two states.

FIG. 2 shows an exploded view of the pen-formed drug delivery device 100 shown in FIG. 1. More specifically, the pen comprises a tubular housing 101 with a window opening 102 and onto which a cartridge holder 110 is fixedly mounted, a drug-filled cartridge 113 being arranged in the cartridge holder. The cartridge holder is provided with distal coupling means 115 allowing a needle assembly 116 to be releasable mounted, proximal coupling means in the form of two opposed protrusions 111 allowing a cap 107 to be releasable mounted covering the cartridge holder and a mounted needle assembly, as well as a protrusion 112 preventing the pen from rolling on e.g. a table top. In the housing distal end a nut element 125 is fixedly mounted, the nut element comprising a central threaded bore 126, and in the housing proximal end a spring base member 108 with a central opening is fixedly mounted. A drive system comprises a threaded piston rod 120 having two opposed longitudinal grooves and being received in the nut element threaded bore, a ring-formed piston rod drive element 130 rotationally arranged in the housing, and a ring-formed clutch element 140 which is in rotational engagement with the drive element (see below), the engagement allowing axial movement of the clutch element. The clutch element is provided with outer spline elements 141 adapted to engage corresponding splines 104 (see FIG. 3B) on the housing inner surface, this allowing the clutch element to be moved between a rotationally locked proximal position, in which the splines are in engagement, and a rotationally free distal position in which the splines are out of engagement. As just mentioned, in both positions the clutch element is rotationally locked to the drive element. The drive element comprises a central bore with two opposed protrusions 131 in engagement with the grooves on the piston rod whereby rotation of the drive element results in rotation and thereby distal axial movement of the piston rod due to the threaded engagement between the piston rod and the nut element. The drive element further comprises a pair of opposed circumferentially extending flexible ratchet arms 135 adapted to engage corresponding ratchet teeth 105 arranged on the housing inner surface. The drive element and the clutch element comprise cooperating coupling structures rotationally locking them together but allowing the clutch element to be moved axially, this allowing the clutch element to be moved axially to its distal position in which it is allowed to rotate, thereby transmitting rotational movement from the dial system (see below) to the drive system. The interaction between the clutch element, the drive element and the housing will be shown and described in greater detail with reference to FIGS. 3A and 3B.

On the piston rod an end-of-content (EOC) member 128 is threadedly mounted and on the distal end a washer 127 is rotationally mounted. The EOC member comprises a pair of opposed radial projections 129 for engagement with the reset tube (see below).

The dial system comprises a ratchet tube 150, a reset tube 160, a scale drum 170 with an outer helically arranged pattern forming a row of dose indicia, a user-operated dial member 180 for setting a dose of drug to be expelled, a release button 190 and a torque spring 155 (see FIG. 3). The dial member is provided with a circumferential inner teeth structure 181 engaging a number of corresponding outer teeth 161 arranged on the reset tube, this providing a dial coupling which is in an engaged state when the reset tube is in a proximal position during dose setting and in a disengaged state when the reset tube is moved distally during expelling of a dose. The reset tube is mounted axially locked inside the ratchet tube but is allowed to rotate a few degrees (see below). The reset tube comprises on its inner surface two opposed longitudinal grooves 169 adapted to engage the radial projections 129 of the EOC member, whereby the EOC can be rotated by the reset tube but is allowed to move axially. The clutch element is mounted axially locked on the outer distal end portion of the ratchet tube 150, this providing that the ratchet tube can be moved axially in and out of rotational engagement with the housing via the clutch element. The dial member 180 is mounted axially locked but rotationally free on the housing proximal end, the dial ring being under normal operation rotationally locked to the reset tube (see below), whereby rotation of the dial ring results in a corresponding rotation of the reset tube 160 and thereby the ratchet tube. The release button 190 is axially locked to the reset tube but is free to rotate. A return spring 195 provides a proximally directed force on the button and the thereto mounted reset tube. The scale drum 170 is arranged in the circumferential space between the ratchet tube and the housing, the drum being rotationally locked to the ratchet tube via cooperating longitudinal splines 151, 171 and being in rotational threaded engagement with the inner surface of the housing via cooperating thread structures 103, 173, whereby the row of numerals passes the window opening 102 in the housing when the drum is rotated relative to the housing by the ratchet tube. The torque spring is arranged in the circumferential space between the ratchet tube and the reset tube and is at its proximal end secured to the spring base member 108 and at its distal end to the ratchet tube, whereby the spring is strained when the ratchet tube is rotated relative to the housing by rotation of the dial member. A ratchet mechanism with a flexible ratchet arm 152 is provided between the ratchet tube and the clutch element, the latter being provided with an inner circumferential teeth structures 142, each tooth providing a ratchet stop such that the ratchet tube is held in the position to which it is rotated by a user via the reset tube when a dose is set. In order to allow a set dose to be reduced a ratchet release mechanism 162 is provided on the reset tube and acting on the ratchet tube, this allowing a set dose to be reduced by one or more ratchet increments by turning the dial member in the opposite direction, the release mechanism being actuated when the reset tube is rotated the above-described few degrees relative to the ratchet tube.

Figure 3A:
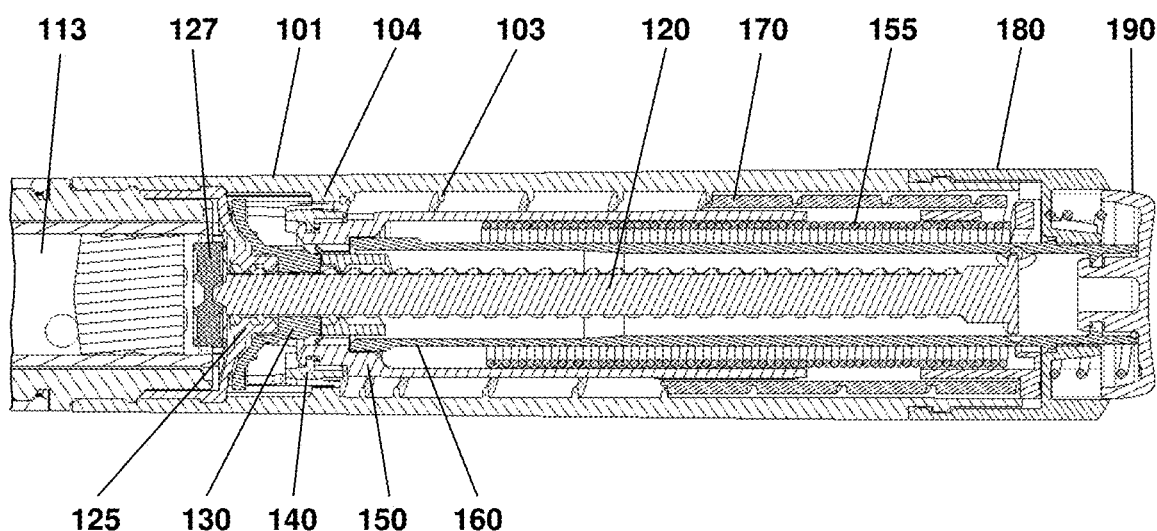

Having described the different components of the expelling mechanism and their functional relationship, operation of the mechanism will be described next with reference mainly to FIGS. 3A and 3B.

The pen mechanism can be considered as two interacting systems, a dose system and a dial system, this as described above. During dose setting the dial mechanism rotates and the torsion spring is loaded. The dose mechanism is locked to the housing and cannot move. When the push button is pushed down, the dose mechanism is released from the housing and due to the engagement to the dial system, the torsion spring will now rotate back the dial system to the starting point and rotate the dose system along with it.

The central part of the dose mechanism is the piston rod 120, the actual displacement of the plunger being performed by the piston rod. During dose delivery, the piston rod is rotated by the drive element 130 and due to the threaded interaction with the nut element 125 which is fixed to the housing, the piston rod moves forward in the distal direction. Between the rubber piston and the piston rod, the piston washer 127 is placed which serves as an axial bearing for the rotating piston rod and evens out the pressure on the rubber piston. As the piston rod has a non-circular cross section where the piston rod drive element engages with the piston rod, the drive element is locked rotationally to the piston rod, but free to move along the piston rod axis. Consequently, rotation of the drive element results in a linear forwards movement of the piston. The drive element is provided with small ratchet arms 134 which prevent the drive element from rotating clockwise (seen from the push button end). Due to the engagement with the drive element, the piston rod can thus only move forwards. During dose delivery, the drive element rotates anti-clockwise and the ratchet arms 135 provide the user with small clicks due to the engagement with the ratchet teeth 105, e.g. one click per unit of insulin expelled.

Turning to the dial system, the dose is set and reset by turning the dial member 180. When turning the dial, the reset tube 160, the EOC member 128, the ratchet tube 150 and the scale drum 170 all turn with it due to the dial coupling being in the engaged state. As the ratchet tube is connected to the distal end of the torque spring 155, the spring is loaded. During dose setting, the arm 152 of the ratchet performs a dial click for each unit dialed due to the interaction with the inner teeth structure 142 of the clutch element. In the shown embodiment the clutch element is provided with 24 ratchet stops providing 24 clicks (increments) for a full 360 degrees rotation relative to the housing. The spring is preloaded during assembly which enables the mechanism to deliver both small and large doses within an acceptable speed interval. As the scale drum is rotationally engaged with the ratchet tube, but movable in the axial direction and the scale drum is in threaded engagement with the housing, the scale drum will move in a helical pattern when the dial system is turned, the number corresponding to the set dose being shown in the housing window 102.

The ratchet 152, 142 between the ratchet tube and the clutch element 140 prevents the spring from turning back the parts. During resetting, the reset tube moves the ratchet arm 152, thereby releasing the ratchet click by click, one click corresponding to one unit IU of insulin in the described embodiment. More specifically, when the dial member is turned clockwise, the reset tube simply rotates the ratchet tube allowing the arm of the ratchet to freely interact with the teeth structures 142 in the clutch element. When the dial member is turned counter-clockwise, the reset tube interacts directly with the ratchet click arm forcing the click arm towards the centre of the pen away from the teeth in the clutch, thus allowing the click arm on the ratchet to move "one click" backwards due to torque caused by the loaded spring.

Figure 3B:
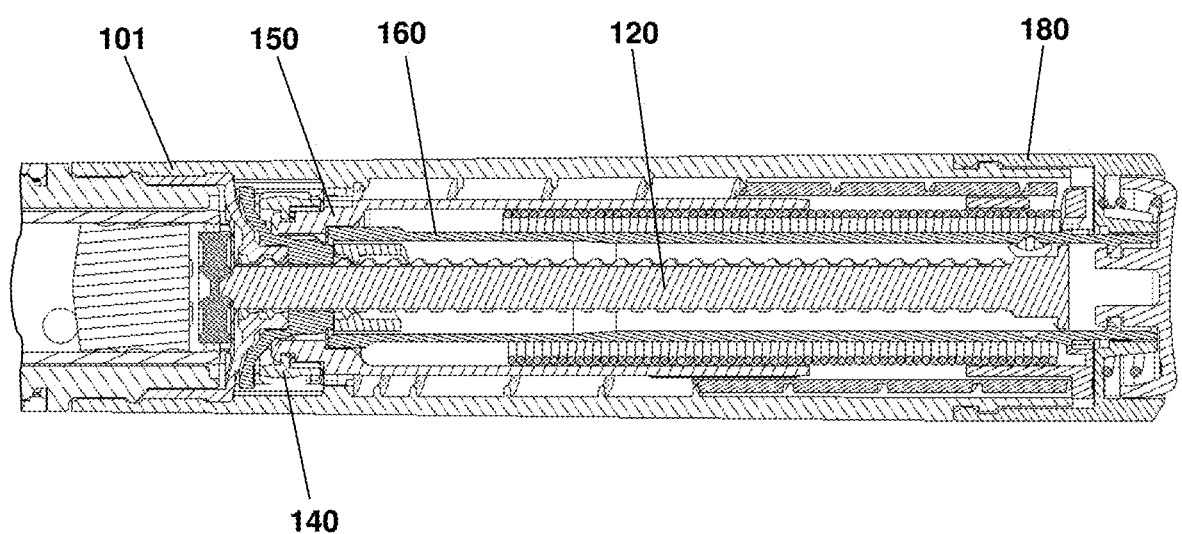

To deliver a set dose, the push button 190 is pushed in the distal direction by the user as shown in FIG. 3B. The dial coupling 161, 181 disengages and the reset tube 160 decouples from the dial member and subsequently the clutch element 140 disengages the housing splines 104. Now the dial mechanism returns to "zero" together with the drive element 130, this leading to a dose of drug being expelled. It is possible to stop and start a dose at any time by releasing or pushing the push button at any time during drug delivery. A dose of less than 5 IU normally cannot be paused, since the rubber piston is compressed very quickly leading to a compression of the rubber piston and subsequently delivery of insulin when the piston returns to the original dimensions.

The EOC feature prevents the user from setting a larger dose than left in the cartridge. The EOC member 128 is rotationally locked to the reset tube, which makes the EOC member rotate during dose setting, resetting and dose delivery, during which it can be moved axially back and forth following the thread of the piston rod. When it reaches the proximal end of the piston rod a stop is provided, this preventing all the connected parts, including the dial member, from being rotated further in the dose setting direction, i.e. the now set dose corresponds to the remaining drug content in the cartridge.

The scale drum 170 is provided with a distal stop surface 174 adapted to engage a corresponding stop surface on the housing inner surface, this providing a maximum dose stop for the scale drum preventing all the connected parts, including the dial member, from being rotated further in the dose setting direction. In the shown embodiment the maximum dose is set to 80 IU. Correspondingly, the scale drum is provided with a proximal stop surface adapted to engage a corresponding stop surface on the spring base member, this preventing all the connected parts, including the dial member, from being rotated further in the dose expelling direction, thereby providing a "zero" stop for the entire expelling mechanism.

To prevent accidental over-dosage in case something should fail in the dialing mechanism allowing the scale drum to move beyond its zero-position, the EOC member serves to provide a security system. More specifically, in an initial state with a full cartridge the EOC member is positioned in a distal-most axial position in contact with the drive element. After a given dose has been expelled the EOC member will again be positioned in contact with the drive element. Correspondingly, the EOC member will lock against the drive element in case the mechanism tries to deliver a dose beyond the zero-position. Due to tolerances and flexibility of the different parts of the mechanism the EOC will travel a short distance allowing a small "over dose" of drug to be expelled, e.g. 3-5 IU of insulin.

The expelling mechanism further comprises an end-of-dose (EOD) click feature providing a distinct feedback at the end of an expelled dose informing the user that the full amount of drug has been expelled. More specifically, the EOD function is made by the interaction between the spring base and the scale drum. When the scale drum returns to zero, a small click arm 106 on the spring base is forced backwards by the progressing scale drum. Just before "zero" the arm is released and the arm hits a countersunk surface on the scale drum.

The shown mechanism is further provided with a torque limiter in order to protect the mechanism from overload applied by the user via the dial member. This feature is provided by the interface between the dial member and the reset tube which as described above are rotationally locked to each other. More specifically, the dial member is provided with circumferential inner teeth structure 181 engaging a number of corresponding outer teeth 161, the latter being arranged on a flexible carrier portion of the reset tube. The reset tube teeth are designed to transmit a torque of a given specified maximum size, e.g. 150-300 Nmm, above which the flexible carrier portion and the teeth will bend inwards and make the dial member turn without rotating the rest of the dial mechanism. Thus, the mechanism inside the pen cannot be stressed at a higher load than the torque limiter transmits through the teeth.

Having described the working principles of a mechanical drug delivery device, embodiments of the present invention will be described.

Figure 4A:
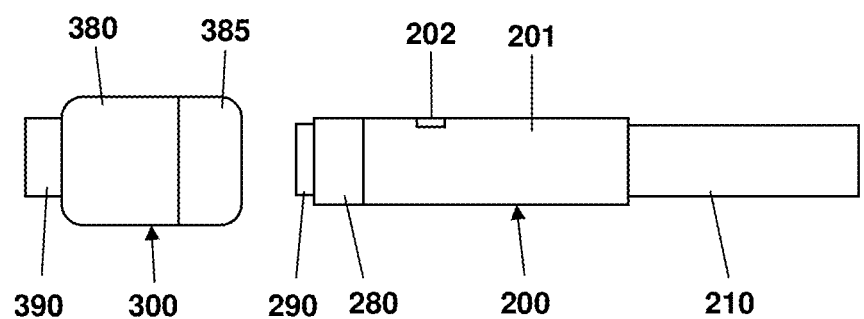
FIGS. 4A and 4B show a schematic representation of an add-on device and a drug delivery device.
Figure 4B:
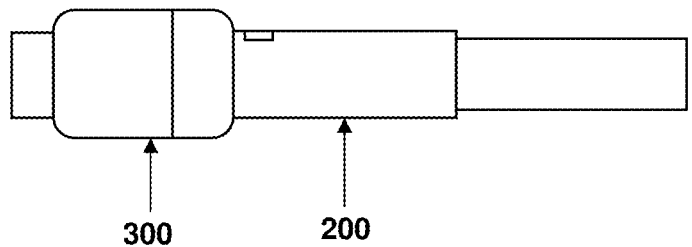

FIGS. 4A and 4B show a schematic representation of a first assembly of a pre-filled pen-formed drug delivery device 200 and a therefor adapted add-on dose logging device 300. The add-on device is adapted to be mounted on the proximal end portion of the pen device housing and is provided with dose setting and dose release means 380 covering the corresponding means on the pen device in a mounted state as shown in FIG. 4B. In the shown embodiment the add-on device comprises a coupling portion 385 adapted to be mounted axially and rotationally locked on the drug delivery housing. The add-on device comprises a rotatable dose setting member 380 which during dose setting is directly or indirectly coupled to the pen dose setting member 280 such that rotational movement of the add-on dose setting member in either direction is transferred to the pen dose setting member. In order to reduce influences from the outside during dose expelling and dose size determination, the outer add-on dose setting member 380 may be rotationally decoupled from the pen dose setting member 280 during dose expelling as will be described in greater detail with reference to the FIG. 5 embodiment. The add-on device further comprises a dose release member 390 which can be moved distally to thereby actuate the pen release member 290. As will be described in greater detail below with reference to FIG. 5 the add-on dose setting member gripped and rotated by the user may be attached directly to the pen housing in rotational engagement therewith.

Alternatively, the shown configuration may be adapted to serve primarily as an aid for people with impaired dexterity to set and release a dose of drug and thus dispense with any dose sensing and dose logging functionality. For such a configuration it is less important that the outer add-on dose setting member is rotationally decoupled from the pen dose setting member 280 during expelling of a dose. Correspondingly, the outer add-on dose setting member may be in permanent rotational engagement with the pen dose setting member 280.

Figure 5:
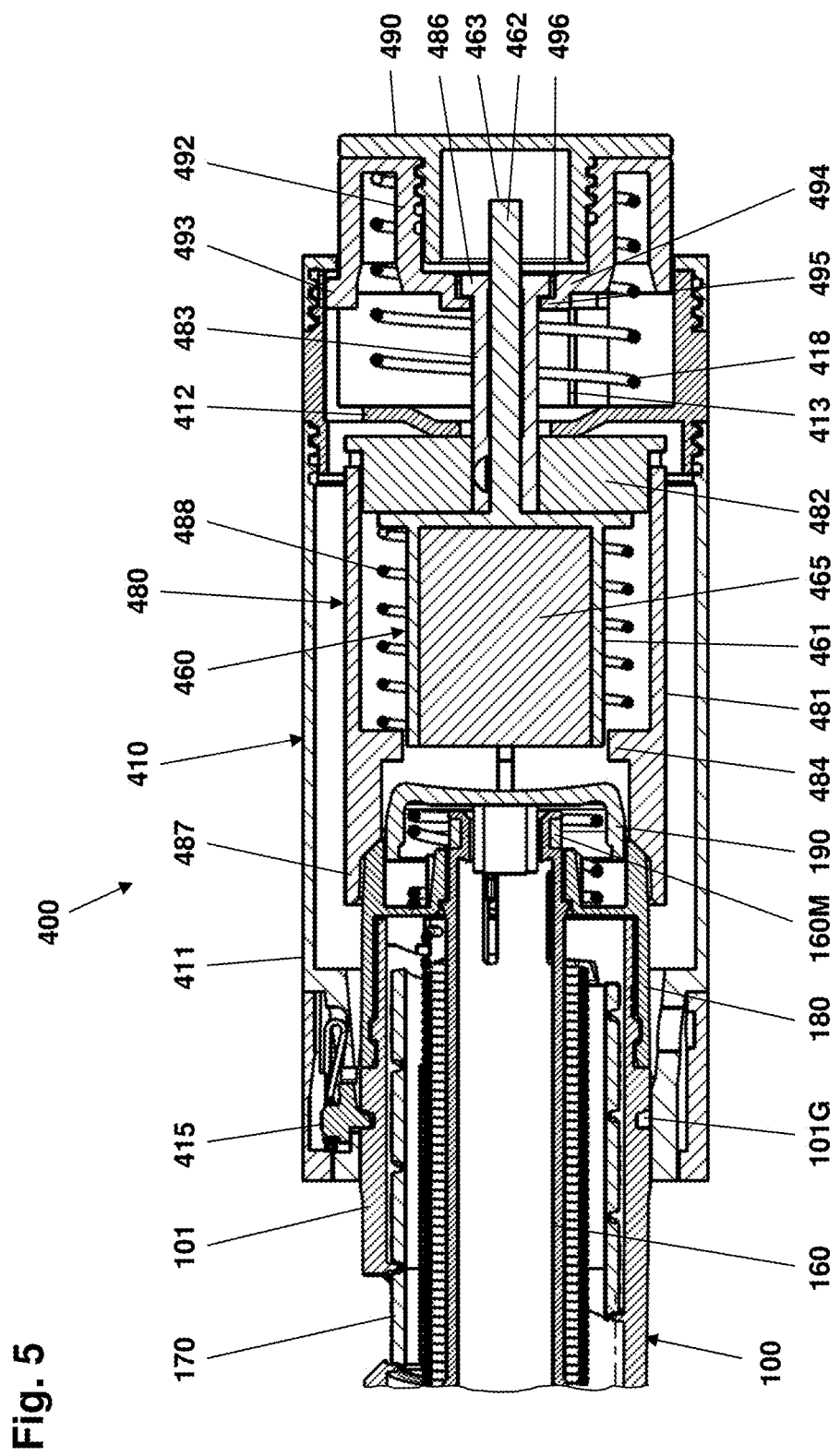
FIG. 5 shows in a cross-sectional view an add-on device mounted on the housing of a drug delivery device.

Turning to FIG. 5 a first exemplary embodiment of an add-on dose logging device 400 adapted to be mounted on a pen-formed drug delivery device 100 will be described in greater detail. The drug delivery device essentially corresponds to the drug delivery device described with reference to FIGS. 1-3 and thus comprises a housing 101, a rotatable dose setting member 180 allowing a user to set a dose amount of drug to be expelled, a release member 190 actuatable between a proximal dose setting position and a distal dose release position, a scale drum 170 as well as a reset tube 160. In order to cooperate with the add-on logging device the drug delivery device has been modified to comprise a generally ring-formed tracer magnet 160M attached to or formed integrally with the reset tube proximal end, the magnet serving as an indicator rotating during expelling of a dose amount, the amount of rotational movement being indicative of the size of the expelled dose amount. Further, the housing has been provided with a circumferential groove 101G just distally of the dose setting member serving as a coupling means for the add-on device.

The add-on device comprises an outer assembly 410 releasably attachable to the drug delivery device housing as well as an inner assembly 480. The inner and outer assemblies are rotationally locked to each other during dose setting, but rotationally de-coupled from each other during dose expelling. The shown embodiment is based on an experimental prototype for which reason some of the structures are formed from a number of assembled parts.

The outer assembly 410 comprises a generally cylindrical housing member 411 defining a general axis for the add-on device and serving as an add-on dose setting member, distally arranged coupling means 415 adapted to engage the coupling groove 101G of the pen housing, and a proximally arranged dose release member 490 coupled to the housing member 411 and axially moveable between an initial proximal position and an actuated distal position. In the shown embodiment the coupling means 415 is in the form of a number of spring-biased coupling members adapted to be releasable received in the housing groove 101G by snap action when the add-on device is slid over the proximal end of the drug delivery device 100, the coupling means thereby axially locking the add-on device to the pen device. The coupling means may be released by e.g. a pulling action or by actuation of a release mechanism. The housing comprises in the proximal portion an inner circumferential flange 412 and a number of axially oriented control grooves 413. The dose release member 490 comprises a number of peripherally arranged axially oriented flanges 493 received in the control grooves 413, the grooves providing a proximal stop against which the dose release member is biased by a first return spring 418 supported between the housing flange 412 and the dose release member 490. The dose release member comprises an inner cylindrical skirt portion 492 with a distal inner flange portion 494, the inner flange portion comprising a distal circumferential lip 495 and a proximal array of axially oriented locking splines 496.

The inner assembly 480 comprises an inner housing 481 and a therein arranged axially moveable sensor assembly 460. The inner housing comprises a proximal wall portion 482 from which a hollow transmission tube 483 extends proximally, an inner circumferential flange portion 484 serving as support for a second biasing spring 488, and a distally extending circumferential skirt portion 487 provided with a number of axially oriented inner projections adapted to be received in the pen dose setting member grooves 182 (see FIG. 1A) to thereby rotationally lock the two members to each other, the engagement allowing some axial play during mounting and operation of the add-on device. The hollow tube 483 comprises at the proximal end a disc-formed portion having a distally facing stop surface adapted to engage the circumferential lip 495 and a circumferential array of axially oriented splines 486 adapted to engage the locking splines 496 on the dose release member 490 to thereby rotationally lock the inner assembly to the dose release member and thus the outer assembly.

The sensor assembly 460 comprises a sensor portion and a proximally extending actuation rod portion 462. The sensor portion comprises a generally cylindrical sensor housing 461 in which the electronic circuitry 465 is arranged (shown schematically in FIG. 5). The sensor housing comprises a distal actuation surface adapted to engage the pen actuation member 190. In the initial dose setting mode (i.e. with the dose release member 490 in the initial proximal position) the sensor housing is biased proximally by the second bias spring 488 into engagement with the inner housing proximal wall portion 482 and with the actuation rod 462 extending from the transmission tube 483 into the interior of the dose release member 490, an axial gap being formed between the proximal end 463 of the actuation rod and an inner actuation surface of the dose release member.

The electronic circuitry 465 comprises electronic components including processors means, one or more sensors, one or more switches, wireless transmitter/receiver means and an energy source. The sensors comprise one or more magnetometers adapted to measure a magnetic field generated by the pen tracer magnet 160M, this allowing rotational movement of the pen reset tube and thus the size of an expelled dose to be determined, see e.g. WO 2014/161952. Further sensor means may be provided allowing the type of the device to be recognized, e.g. a light emitter and a colour sensor adapted to determine the colour of the pen release member, the colour serving as an identifier for the drug type contained in the prefilled pen device. The processor means may be in the form of a generic microprocessor or an ASIC, non-volatile program memory such as a ROM providing storage for embedded program code, writable memory such as flash memory and/or RAM for data, and a controller for the transmitter/receiver.

In a situation of use with the add-on device 400 mounted on the pen drug delivery device 100 as shown in FIG. 5, the user starts setting a desired dose by rotating the housing member 411 (i.e. the add-on dose setting member) and with that also the dose release member 490. During dose setting the dose release member is biased towards its initial proximal position whereby it is rotationally locked to the inner assembly 480 via the locking splines 486, 496, this allowing the rotational movement of the add-on dose setting member to be transferred to the inner housing 461 and thus the pen dose setting member 180.

When a dose has been set the user will actuate the dose release member 490 by moving it distally against the force of the first bias spring 418. During the initial release movement the locking splines 486, 496 will disengage, this rotationally de-coupling the inner assembly 480 from the dose release member and thus from the add-on dose setting housing member 411. During the further release movement the dose release member 490 engages the actuation rod proximal end 463 whereby the sensor assembly 460 during the further release movement will be moved distally towards the pen dose release member 190 and subsequently into contact with the pen release member. The engaging surfaces of the actuation rod 462 and the add-on dose release member 490 are optimized for minimal transfer of rotational movement. Finally, further distal movement of the add-on release member 490 will result in actuation of the pen release member 190 and thereby expelling of the set dose, the sensor assembly 460 thereby serving as an actuator.

In order to determine the size of an expelled dose the amount of rotation of the tracer magnet 160M and thus the reset tube 160 is determined. More specifically, initial movement of the sensor assembly will activate a sensor switch (not shown) which in turn will activate the sensor electronics 465 and start sampling of data from the magnetometers, this allowing a rotational start position of the tracer magnet 160M to be determined prior to release of the expelling mechanism. During this period also the colour of the pen release member and thus the type of drug contained in the cartridge may be determined. As the reset tube may rotate more than 360 degrees during expelling of a dose of drug, rotational movement during expelling will be detected and the number of full rotations (if any) determined. When it is detected that rotation of the reset tube has stopped, e.g. when a set dose has been fully expelled or when out-dosing is paused by the user, a rotational end position will be determined, this allowing the size of an expelled dose to be determined. Alternatively, the rotational end position may be determined when the sensor switch detects that the sensor assembly 460 has returned to its initial position.

As appears, due to the rotational un-coupling of the inner assembly 460 from the outer assembly 480 during drug expelling, it is prevented to a high degree that movements of the outer parts of the add-on device will negatively influence the precise determination of rotational movement and rotational positions of the reset tube 160.

The determined dose size will be stored together with a time stamp and, if detected, a drug type identifier in a log memory. The content of the log memory may then be transmitted by NFC, Bluetooth® or other wireless means to an external device, e.g. a smartphone, which has been paired with the add-on logging device. An example of a suitable pairing process is described in EP application 17178059.6 which is hereby incorporated by reference.

Figure 6:
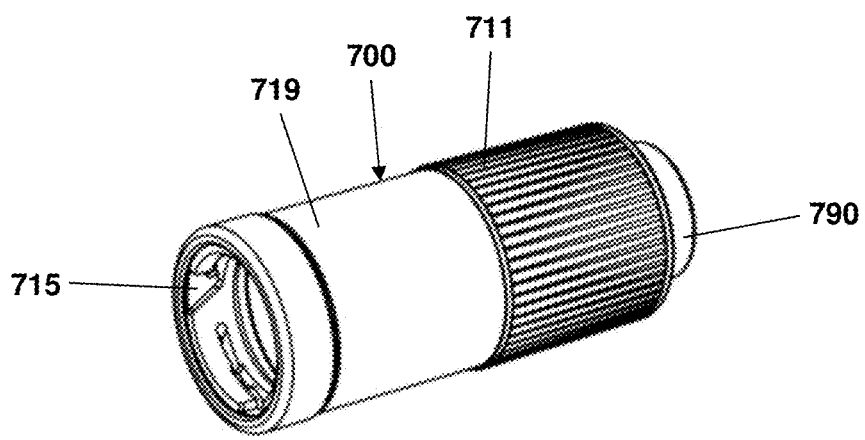
FIG. 6 shows a further embodiment of add-on device in combination with a drug delivery device.
Figure 6:
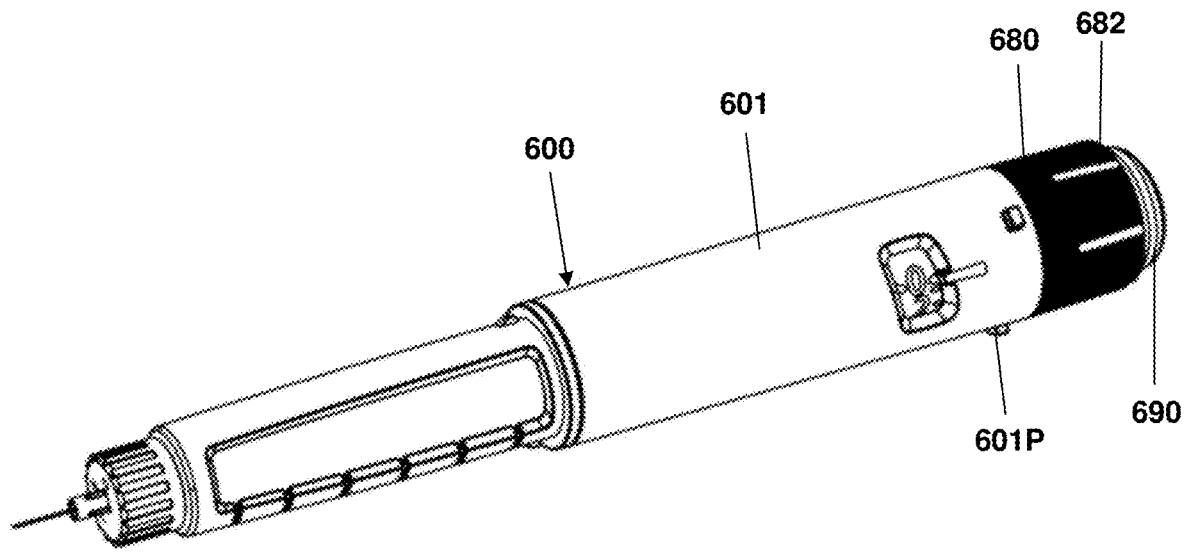

Turning to FIG. 6 a second exemplary embodiment of an add-on dose logging device 700 adapted to be mounted on a pen-formed drug delivery device 600 will be described in greater detail. The drug delivery device essentially corresponds to the drug delivery devices described with reference to FIGS. 1-3 and thus comprises a housing 601, a rotatable dose setting member 680 allowing a user to set a dose amount of drug to be expelled, a release member 690 actuatable between a proximal dose setting position and a distal dose release position, a scale drum 670 as well as a reset tube 660. In order to cooperate with the add-on logging device 700 the drug delivery device has been modified to comprise a generally ring-formed magnet 660M attached to or formed integrally with the reset tube proximal end, the magnet serving as an indicator rotating during expelling of a dose amount, the amount of rotational movement being indicative of the size of the expelled dose amount. Further, the housing has been provided with a number of protrusions 601P just distally of the dose setting member serving as a coupling means for the add-on device. In the shown embodiment three coupling protrusions are located equidistantly on the housing.

The add-on device 700 comprises an outer assembly 710 releasably attachable to the drug delivery device housing as well as an inner assembly (see below). The outer assembly 710 comprises a generally cylindrical distal coupling portion 719 (as in the embodiment of FIG. 4A) defining a general axis for the add-on device and being adapted to be mounted axially and rotationally locked on the drug delivery housing by means of a number of bayonet coupling structures 715 adapted to engage the corresponding coupling protrusions 601P on the pen housing and releasably snap into engagement. The add-on device further comprises a proximal dose setting member 711 mounted freely rotatable on the coupling portion and which like in the embodiment of FIG. 5 is coupled to the pen dose setting member 680 such that rotational movement of the add-on dose setting member 711 in either direction is transferred to the pen dose setting member. The add-on device further comprises a dose release member 790 which during dose setting rotates with the dose setting member. A first biasing spring 718 supported on an inner circumferential flange 712 on the dose setting member provides a proximally directed biasing force on the dose release member. As in the embodiment of FIG. 5 the inner and outer assemblies are rotationally locked to each other during dose setting, but rotationally de-coupled from each other during dose expelling.

The inner assembly 780 generally corresponds to the inner assembly 480 of the FIG. 5 embodiments and thus generally comprises the same structures providing the same functionality. Correspondingly, the inner assembly comprises (see FIG. 7A) inner housing 781 and a therein arranged axially moveable sensor assembly 760. The inner housing comprises a proximal wall portion 782 from which a hollow transmission tube structure 783 extends proximally, a distal inner circumferential flange portion 784 serving as support for a second biasing spring 788, and a distally extending circumferential skirt portion 787 adapted to engage the pen dose setting member grooves 682 (see FIG. 6) to thereby rotationally lock the two members to each other, the engagement allowing some axial play during mounting and operation of the add-on device. The hollow tube 783 comprises at the proximal end a number of flange portions 786 having distally facing stop surfaces adapted to engage a circumferential inner flange 795 of the dose release member 790, as well as a number of axially oriented splines adapted to engage the locking splines 796 on the dose release member 790 to thereby rotationally lock the inner assembly to the dose release member and thus the outer assembly.

The sensor assembly 760 comprises a sensor portion and a proximally extending actuation rod portion 762. The sensor portion comprises a generally cylindrical sensor housing 761 in which the electronic circuitry 765 (see below) is arranged. The sensor housing comprises a distal spacer cap 764 covering the magnet sensors and being adapted to engage the pen actuation member 690. In the initial dose setting mode (i.e. with the dose release member 790 in the initial proximal position) the sensor housing is biased proximally by the second bias spring 788 into engagement with the inner housing proximal wall portion 782 and with the actuation rod 762 extending from the transmission tube 783 into the interior of the dose release member 790, an axial gap being formed between the proximal end 763 of the actuation rod and an inner actuation surface of the dose release member.

The electronic circuitry 765 comprises electronic components including processor means, sensors, an axial switch, e.g. a dome switch actuated by an axial force exerted on the actuation rod portion 762, wireless transmitter/receiver means and an energy source. More specifically, in the shown embodiment the electronic circuitry 765 comprises a layered construction comprising, from the distal end, a first PCB 766 on which a number of sensor components, e.g. magnetometers 766M, are arranged, a pair of battery connector discs 767 for a pair of coin cells, a second PCB 768 on which the majority of the electronic components are mounted (e.g. processor, transmitter/receiver and memory), and an upper disc 769 with a slot allowing the actuation rod portion 762 to be received, the five members being interconnected by flexible ribbon connectors.

The sensors comprise a number of magnetometers adapted to measure a magnetic field generated by the pen magnet 660M, this allowing rotational movement of the pen reset tube and thus the size of an expelled dose to be determined, see e.g. WO 2014/0161952. Further sensor means may be provided allowing the type of the device to be recognized, e.g. a light emitter and a colour sensor adapted to determine the colour of the pen release member, the colour serving as an identifier for the drug type contained in the prefilled pen device. The colour sensor and light emitter may operate with visible (to the human eye) light or light fully or partly outside the visible spectrum. The processor means may be in the form of a generic microprocessor or an ASIC, non-volatile program memory such as a ROM providing storage for embedded program code, writable memory such as flash memory and/or RAM for data, and a controller for the transmitter/receiver.

In a situation of use with the add-on device 700 mounted on the pen drug delivery device 600, the user starts setting a desired dose by rotating the dose setting member 711 (i.e. the add-on dose setting member) and with that also the dose release member 790. During dose setting the dose release member is biased towards its initial proximal position whereby it is rotationally locked to the inner assembly 780 via the locking splines 786, 796, this allowing the rotational movement of the add-on dose setting member to be transferred to the inner housing 761 and thus the pen dose setting member 680.

When a dose has been set the user will actuate the dose release member 790 by moving it distally against the force of the first bias spring 718. During the initial release movement the locking splines 786, 796 will disengage, this rotationally de-coupling the inner assembly 780 with the electronics from the dose release member 790 and thus from the add-on dose setting member 711. During the further release movement the dose release member 790 engages the actuation rod proximal end 763 (see FIG. 8 A) whereby the sensor assembly 760 during the further release movement will be moved distally towards the pen release member 690 and subsequently into contact with the pen release member (see FIG. 8 B). The engaging surfaces of the actuation rod 762 and the add-on dose release member 790 are optimized for minimal transfer of rotational movement. Finally, further distal movement of the add-on release member 790 will result in actuation of the pen release member 690 (see FIG. 8 C in which the reset tube outer teeth 661 has been moved distally) and thereby expelling of the set dose (see FIG. 8 D), the sensor assembly 760 thereby serving as an actuator.

In order to determine the size of an expelled dose the amount of rotation of the magnet 660M and thus the reset tube 660 is determined. More specifically, initial movement of the sensor assembly will activate a sensor switch 769 which in turn will activate the sensor electronics 765 and start sampling of data from the magnetometers, this allowing a rotational start position of the magnet 660M to be determined prior to release of the expelling mechanism. During this period also the colour of the pen release member and thus the type of drug contained in the cartridge may be determined. As the reset tube 660 may rotate more than 360 degrees during expelling of a dose of drug, rotational movement during expelling will be detected and the number of full rotations (if any) determined. When it is detected that rotation of the reset tube has stopped, e.g. when a set dose has been fully expelled or when out-dosing is paused by the user, a rotational end position will be determined, this allowing the size of an expelled dose to be determined. Alternatively, the rotational end position may be determined when the sensor switch detects that the sensor assembly 760 has returned to its initial position.

As appears, due to the rotational un-coupling of the inner assembly 760 from the outer assembly 780 during drug expelling, it is prevented to a high degree that movements of the outer parts of the add-on device will negatively influence the precise determination of rotational movement and rotational positions of the reset tube 660.

Figure 7A:
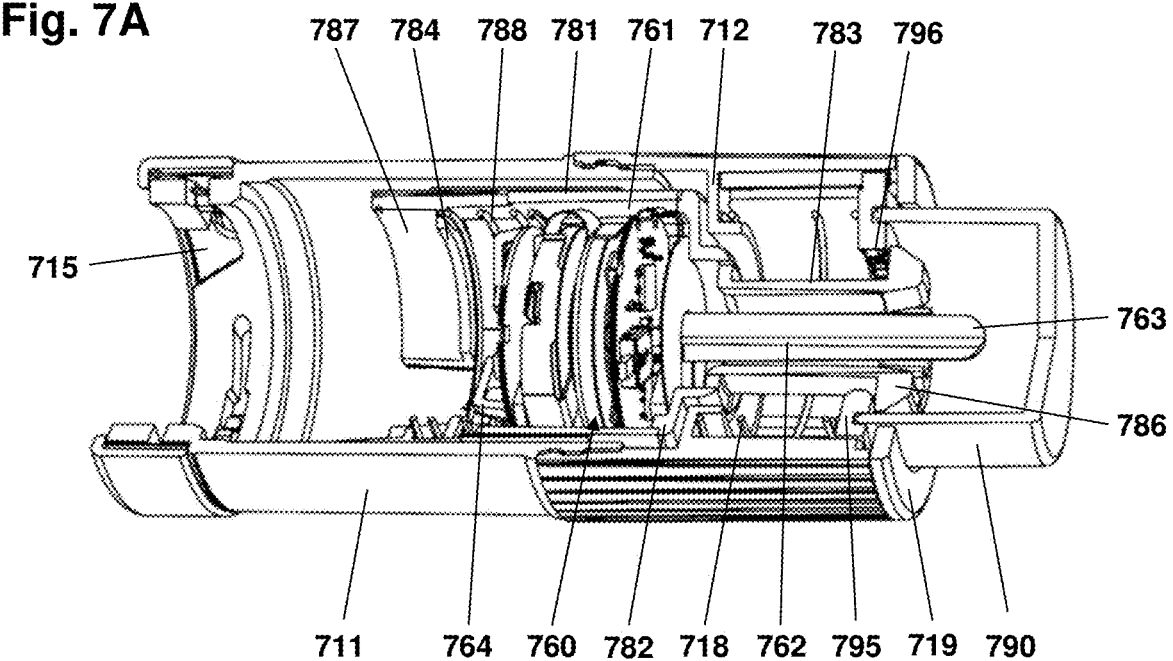
FIGS. 7A and 7B show cross-sectional views of the add-on device of FIG. 6.

Having described the mechanical concept and working principle of the add-on dose logging devices of FIGS. 5 and 7A, the sensor and tracer system per se will be described in greater detail. Basically, the sensor and tracer system comprises a moving magnetic tracer component and a sensor system comprising one or magnetometers, e.g. 3D compass sensors.

Figure 9:
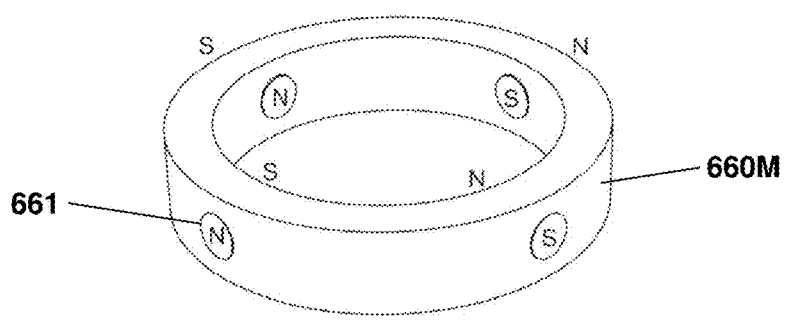
FIG. 9 shows individual dipole magnets arranged equidistantly in a ring-formed tracer component.

In an exemplary embodiment the magnetic tracer component is in the form of a multi-pole magnet having four poles, i.e. a quadrupole magnet. In FIG. 9 four dipole standard magnets 661 have been arranged equidistantly in a ring-formed tracer component 660M, the four separate dipole magnets providing a combined quadrupole magnet with the four poles offset by 90 degrees. Indeed, each of the dipole magnets are formed by a very large number of individual magnetic particles oriented in the same direction. The individual magnets may be arranged in the same plane or may be axially offset from each other.

Figure 10A:
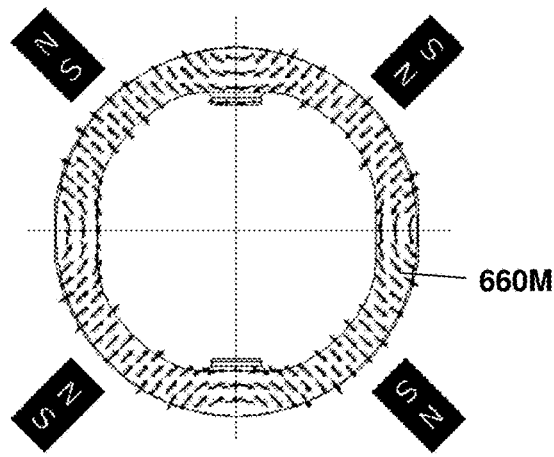
FIG. 10A shows a tracer component manufactured from a magnetisable material in combination arranged between individual magnets.
Figure 10B:
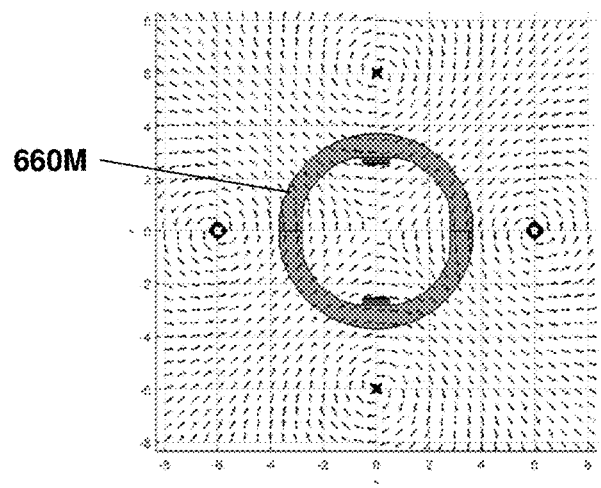
FIG. 10B shows a tracer component manufactured from a magnetisable material arranged in a multipolar electromagnetic field.

Alternatively, a multi-pole magnet 660M can be created by magnetization of a magnetisable material either by use of individual powerful magnets (FIG. 10A) or through use of electromagnetic fields (FIG. 10B).

Figure 7B:
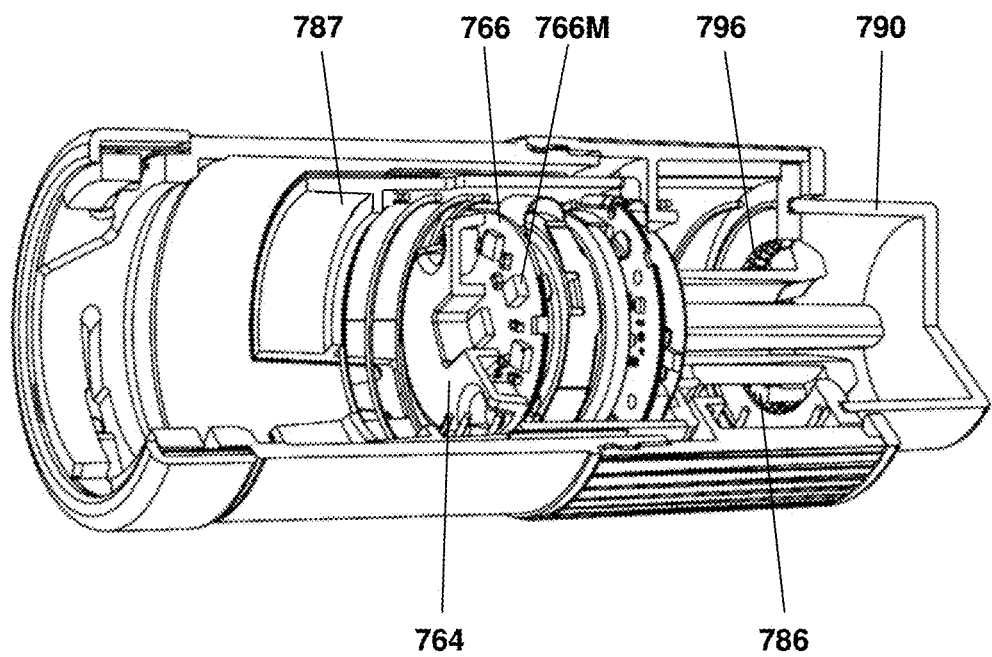
Figure 7C:
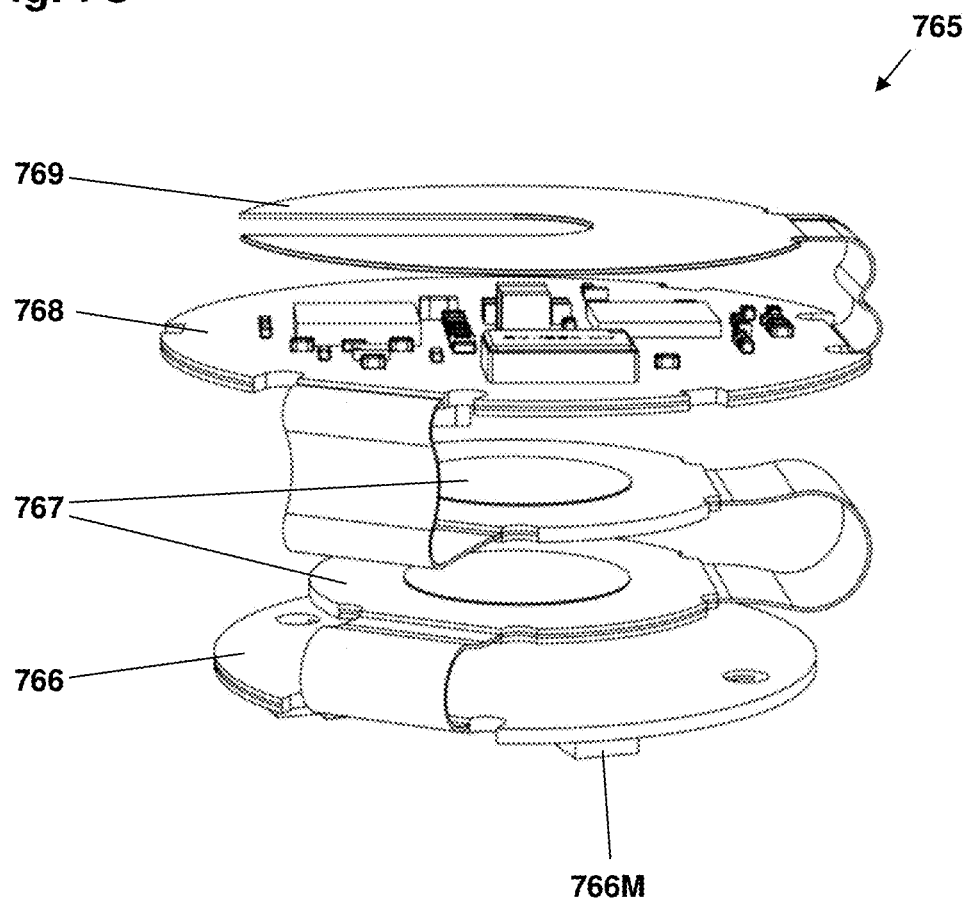
FIG. 7C shows in detail the electronic sensor circuitry incorporated in the add-on device of FIG. 7A, FIGS. 8A-8D show in sectional views and in different operational states an assembly comprising the add-on device of FIG. 6 mounted on a drug delivery device.
Figure 11:
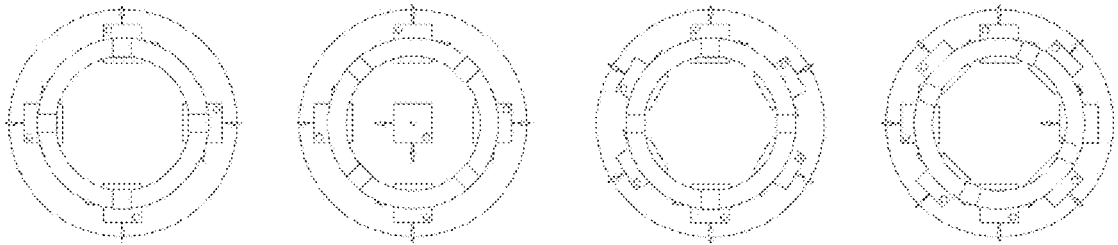
FIG. 11 shows different embodiments of a sensor system comprising magnetometers arranged relative to a tracer component 660M.
Figure 11:
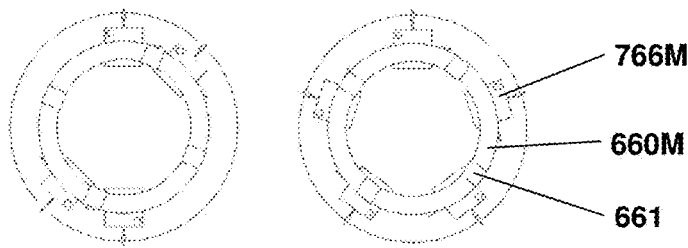

A given sensor system may be using e.g. 4, 5, 6 or 8 magnetometers 766M arranged relative to a tracer component 660M as illustrated in FIG. 11. The sensors may be arranged in the same plane, e.g. as shown in FIG. 7B, or they may be axially offset from each other. The more sensors, the smaller spacing between the sensors and thus more data with a better signal-to-noise ratio can be gathered. However, the more sensors, the more data processing is required and the more power is consumed.

In some cases, not only disturbances from external fields need to be handled. The torque-providing spring for driving the dose expelling motor in the disposable device as described above may be magnetized when subjected to an external magnetic field and thus provide an internal disturbing magnetic field.

Where external disturbances may be cancelled out to a large extent by signal processing algorithms, because they influence all the sensors more or less equally and in the same direction, a magnetized torque spring will influence the sensors much like the tracer magnet and therefore be more likely to offset the measurements and cause errors.

Figure 12A:
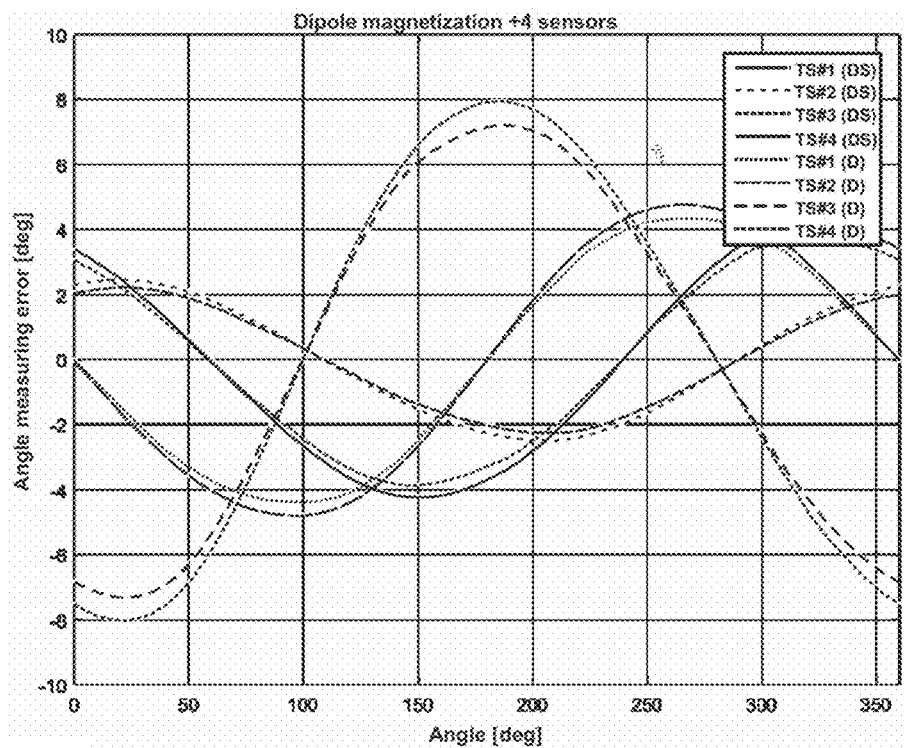
FIG. 12A shows angle measurements for a dipole tracer magnet in combination with a first sensor set-up.
Figure 12B:
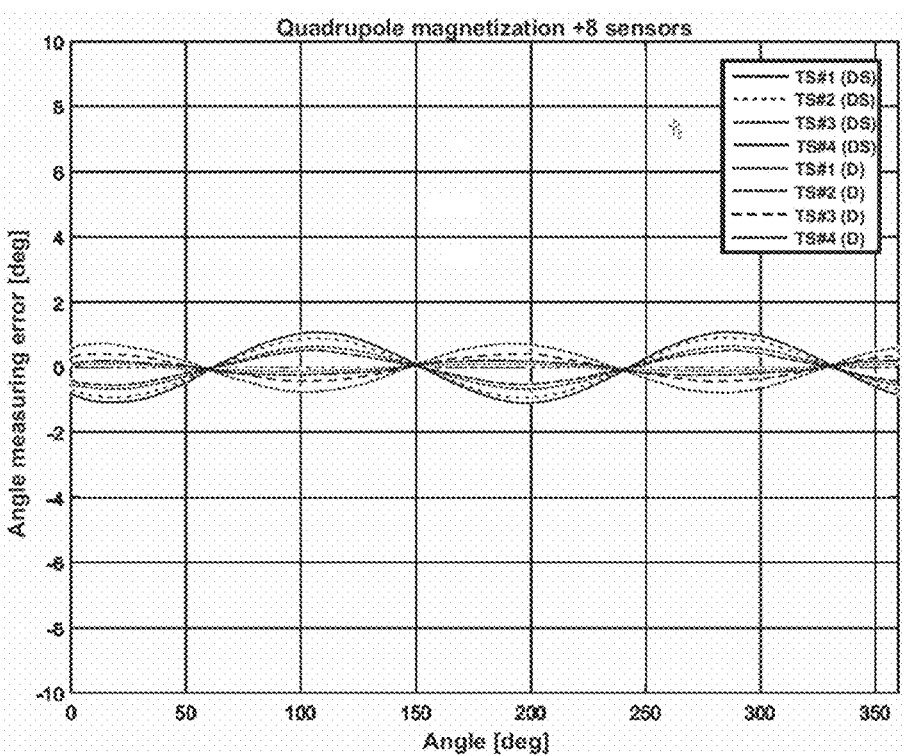
FIG. 12B shows angle measurements for a quadrupole tracer magnet in combination with a second sensor set-up.

However, as it can be seen from FIGS. 12A and 12B the use of a quadrupole tracer magnet instead of a dipole tracer magnet, significantly reduce the error in determining the position of the tracer magnet.

More specifically, FIGS. 12A and 12B show simulations of the influence of a magnetized torque spring at four different levels of magnetization (TS1-TS4) for both dose-setting (DS) and out-dosing (D). FIG. 12A illustrates the calculated angle measuring error (i.e. the difference between the calculated angle and the true angle) for a dipole tracer magnet in combination with a 4 sensors set-up, and FIG. 12B illustrates the calculated angle measuring error for a quadrupole tracer magnet in combination with an 8 sensors set-up. Due to the sensors being closer to the tracer magnet during out-dosing (see e.g. FIGS. 8A and 8C) the angle error is slightly smaller during out-dosing. This said, in the above-described embodiment sensor measurements take place only during out-dosing. For the quadrupole tracer magnet 8 sensors were used as the smaller circumferential spacing between the individual poles in the quadrupole tracer magnet provides a higher input rate to the sensor system which can be more precisely captured by 8 instead of 4 sensors, however, comparable results would be expected for a quadrupole tracer magnet in combination with a 4 sensors set-up. As appears, use of a quadrupole tracer magnet reduces the angle error from ca. 4-8 degrees to ca. 0.5-1 degrees, roughly a factor of 8.

In the shown FlexTouch® drug delivery device the reset tube 660 and thus the tracer magnet 660M rotates 7.5 degrees for each unit of insulin expelled. Thus, a possible angle error in the 4-8 degrees range may result in an incorrect determination of the expelled dose amount.

The quadrupole tracer magnet is thus not only reducing the systems sensitivity to disturbances from external fields, but also from internal fields. This is an important aspect of using a multipole tracer magnet, since traditional magnetic shielding of external sources by use of an iron-containing metallic sheet may be used to reduce the influence of external fields, but may not be possible to fit between the tracer magnet and an internal disturbing magnetic field. Further, incorporating a magnetic shield would take up space and introduce additional costs.

Alternatively, this may be mitigated by using a spring of a non-magnetisable material, however, current spring-driven pens on the market today comprise a magnetisable torque spring and replacement may not be feasible due to other requirements of the spring.

Having described the structural set-up for a sensor assembly incorporating a rotating quadrupole tracer magnet, in the following an exemplary method of determining actual movements for such an assembly will be described.

Figure 13:
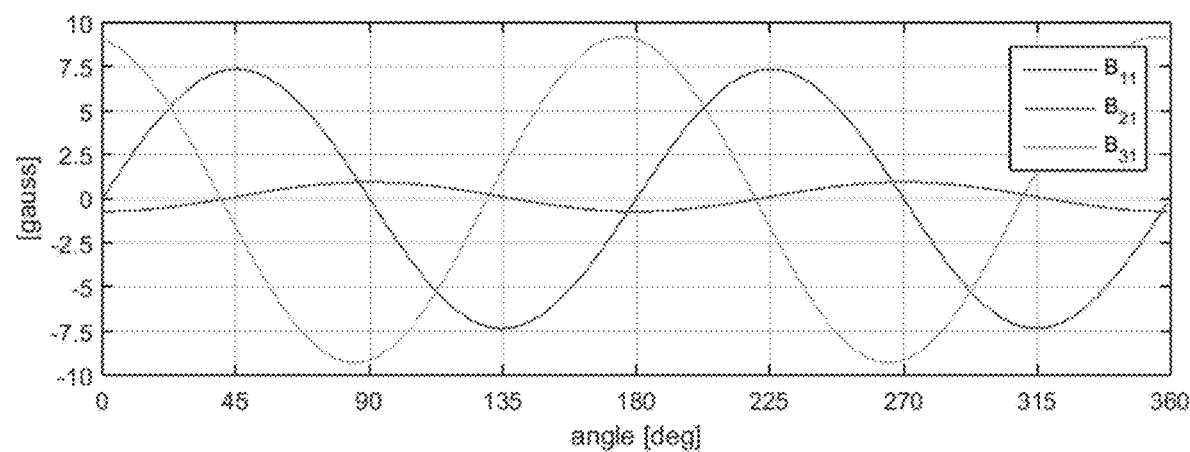
FIG. 13 shows signals from a quadrupole magnet over one full revolution of the magnet.

The signal from the quadrupole magnet is periodic with a period two over one full revolution of the magnet. This can be seen from FIG. 13 where the tangential, radial and axial field level is pictured.

Figure 14:
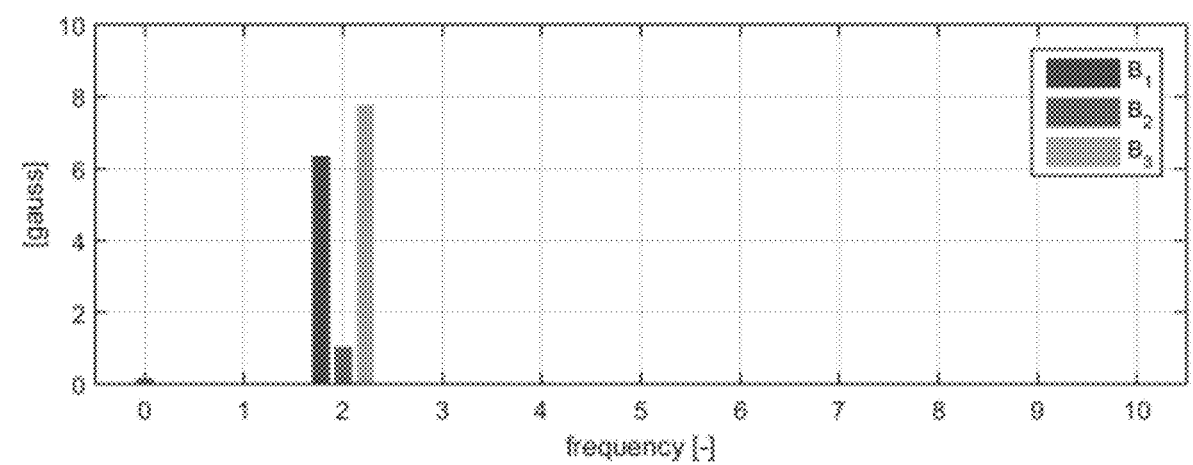
FIG. 14 shows a map of the frequency components of the signal from FIG. 13.

Mapping the frequency components of the signal, it is seen that all most the entire signal from the magnet fits into the frequency two signal, see FIG. 14.

Figure 15:
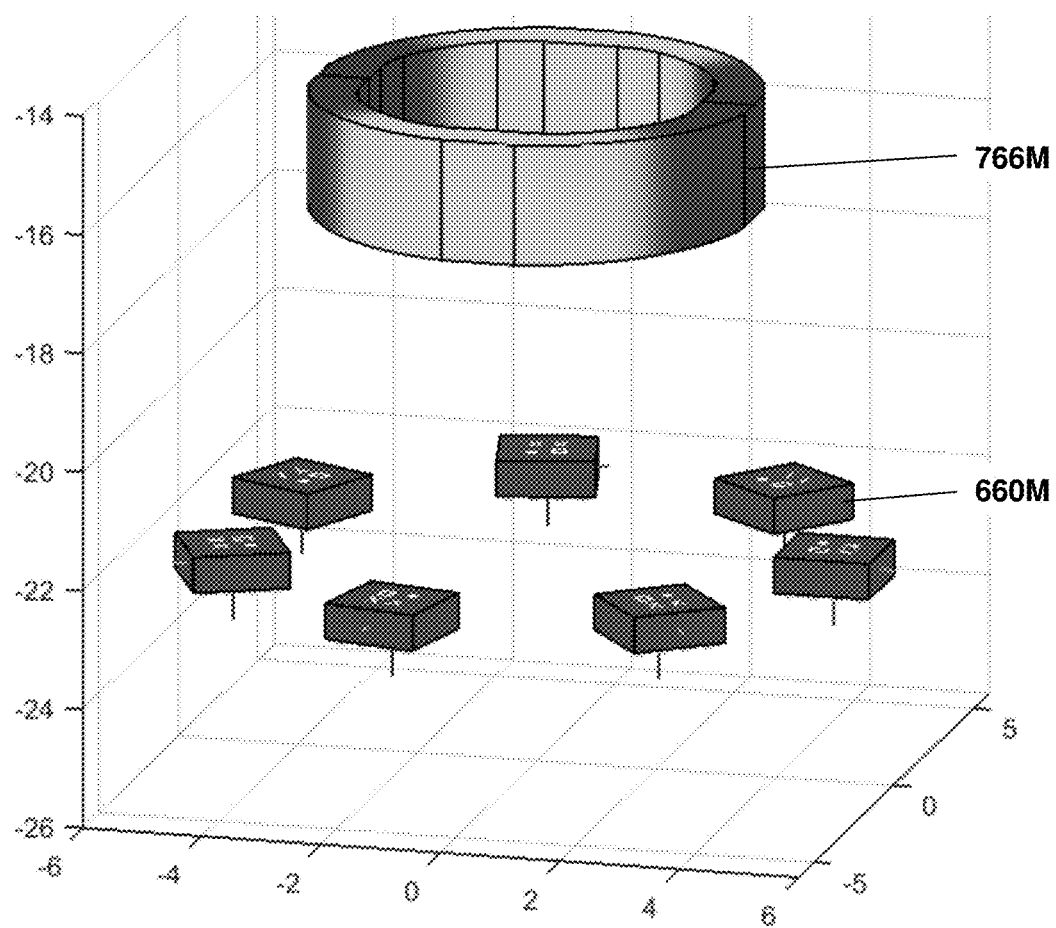
FIG. 15 shows an assembly of a quadrupole magnet and 7 magnetometers.

To determine a dose size utilizing at the quadrupole field, it is necessary to determine the static start and end angle of the quadrupole magnet. Since the magnet is static before and after the dose has been delivered, the field is sampled over space instead of sampled over time. In an exemplary embodiment a measurement system is configured with N=7 sensors with circular layout and equal spacing, see FIG. 15 showing sensor 766M placements relative to the quadrupole magnet 660M.

In order to determine the orientation or the magnet, a discrete Fourier transform (DFT) is computed on the field measured in the sensors $$\hat{B}_{jn} = \frac{2}{N}\sum_{k=1}^{N} B_{jk}\exp(-2\pi i k n/N).$$

Here $B_{jk}$ is the field in the j'th channel of the k'th sensor, j=1 is tangential field, j=2 is radial, and j=3 is axial, $i=\sqrt{-1}$ is the imaginary unit, and $\hat{B}_{jn}$ is the n'th frequency component of the signal in the j'th channel.

As described above, the signal from the quadrupole magnet is a period n=2 signal, and therefore we can determine the orientation of the magnet relative to the sensor board by looking at the phase of $\hat{B}_{j2}$, $$\varphi_j = \text{atan } 2[\text{Im}(\hat{B}_{j2}), \text{Re}(\hat{B}_{j2})]/2.$$

Because the samples of sines and cosines at different frequencies are orthogonal, any disturbance to the signal that is, e.g., period n=0, 1 or 3, will be filtered out by the Fourier transform.

This relates to both external as internal disturbances. An internal component in an auto-dose pen-injector is the metal torsion spring to drive the dosing mechanism. In the case of this being magnetized, the spring field will primarily look like a period 1 signal at the sensors position. External disturbances like a dipole magnet in the vicinity of the sensors will also tend to have a signal with period 0 or 1. Using the DFT, it is possible to filter out the disturbances from other frequencies and only determining the magnet orientation from the frequency 2 signal.

The combination of a quadrupole magnet and the DFT is therefore superior compared to a dipole magnet whose period 1 signal is similar to the frequency of common disturbances.

Using a DFT based algorithm gives a larger freedom to choose an arbitrary number of sensors, compared to a lookup based algorithm. The chosen number of sensors is preferably at least 5 due to the Nyquist sampling theorem. Besides that the number of sensors can be freely and actively used in order to filter out specific frequencies of the signal to prevent aliasing effects. Use of 3-axis "compass" magnetometers allow radial, tangential, and axial signals to be measured, however, analysis has shown that the radial field component is most sensitive to mechanical eccentricity and tilt (out of plane angle between magnet and sensors), or it could be said the symmetrical sensor arrangement is not as efficient at the eliminating the impact of those mechanical misalignments for the radial field signal as for the two others. Correspondingly, in an exemplary embodiment the radial field is not measured and only tangential and axial field values are utilized.

Because the tangential and axial signals are just different vector components of the same magnetic field lines, they are strongly related: The tangential signal is precisely 90 degrees out of phase with the axial signal. The phase angle can be calculated individually from the tangential and axial signal, and the 90.0 degrees phase correction can be made to the result from the tangential signal. The two values must be approximately equal.

If they are not entirely equal it may be due to small magnetic disturbances from the electronic components in the device, or from sensor inaccuracy. Exemplary sensors used have up to +/−10% error. To suppress noise the average of the two angle measurements from on axial and tangential field can be used.

However, if there is a "large" difference between the phase angle computed from the tangential and axial field signal, it is a sign that the magnetic disturbance is large, e.g., from a telephone/headphone/magnetic finger ring very close to or forced against the memory device.

Thus the difference between phase angle from tangential and axial signal can be used as a quality indicator. For example, for a given exemplary embodiment up to around 4 degrees can be expected due to tolerances on the mechanical and electrical system, however, if the difference exceeds 5 degrees it can be taken as a sign that there is a large disturbance and the measurement is unreliable, and then it may be decided to indicate a fail event and not report a dose measurement, but only that a dose was taken at a given time point.

In the above disclosure the issue of both external disturbing magnet fields as well as an internal disturbing magnet field from the pen device torque spring have been addressed by the use of a quadrupole tracer magnet in combination with a sensor array comprising a number of magnetometers. In the following this issue is addressed by a different approach which may be used as an alternative or in addition to the above-described quadrupole design.

Using magnetic shields to shield magnetic systems from outside interference is commonly known and used. Normally shields are used as a barrier to either contain magnetic fields and prevent them from influencing other systems, or as a barrier to contain a system and shield it from being influenced by outside (unshielded) magnetic fields. Internal components of the system, that may introduce disturbing fields, are normally placed outside the shielded volume of the system. Indeed, it may be possible to incorporate a shield in a drug delivery device comprising a drive spring manufactured from a magnetisable material, however, as this may require a major redesign of the pen device this may not be a cost-effective option.

The technical problem to be solved, is thus to provide a magnetic shield preventing/reducing internal magnetic fields from disturbing the measurements of the magnetic sensors in a capturing device or assembly based on magnetometers. Additionally, such a shield may also serve to prevent/reduce the disturbances from "normal" external magnetic fields.

The suggested solution is to introduce a shield of mu-metal, to not only shield the sensor system from external magnetic fields, but also divert any unintended internal magnetic field introduced by the torque spring towards the shield and reduce the disturbance of the field of the tracer magnets. By reducing the strength of the disturbing field from the torque spring it may enable the use of fewer sensors and thus lower signal processing requirements to obtain required accuracy and redundancy, and thereby reduce both costs and power consumption.

Mu-metal is a nickel-iron soft magnetic alloy with very high permeability. It has several compositions, with approximately 80% nickel, 15% a few percent molybdenum and in some compositions a little copper and chromium. Mu-metal is very ductile and workable and can easily be formed into thin sheets needed for magnetic shields. However, mu-metal objects require heat treatment after they are worked into their final form.

Magnetic shields made with mu-metal works by providing a path for the magnetic lines around the shielded area instead of blocking them. The mu-metal sort of offers an "easier" path than thought the air with much lower relative permeability and thus diverts the magnetic field. However, mu-metal has a much lower saturation level and are thus not suitable for shielding against stronger magnetic fields.

Figure 8A:
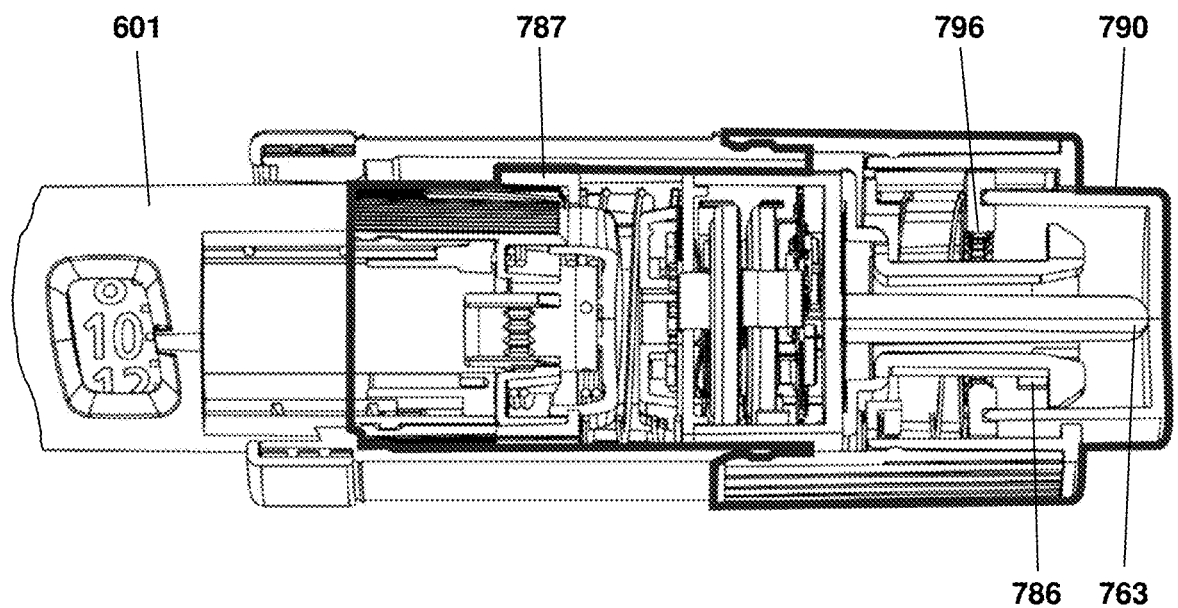
Figure 8B:
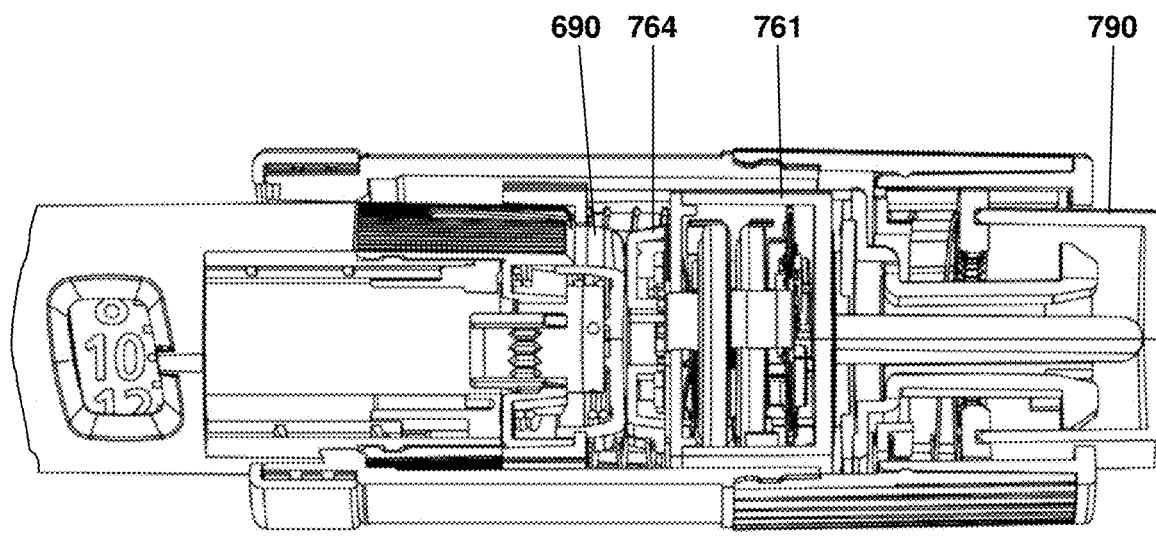
Figure 8C:
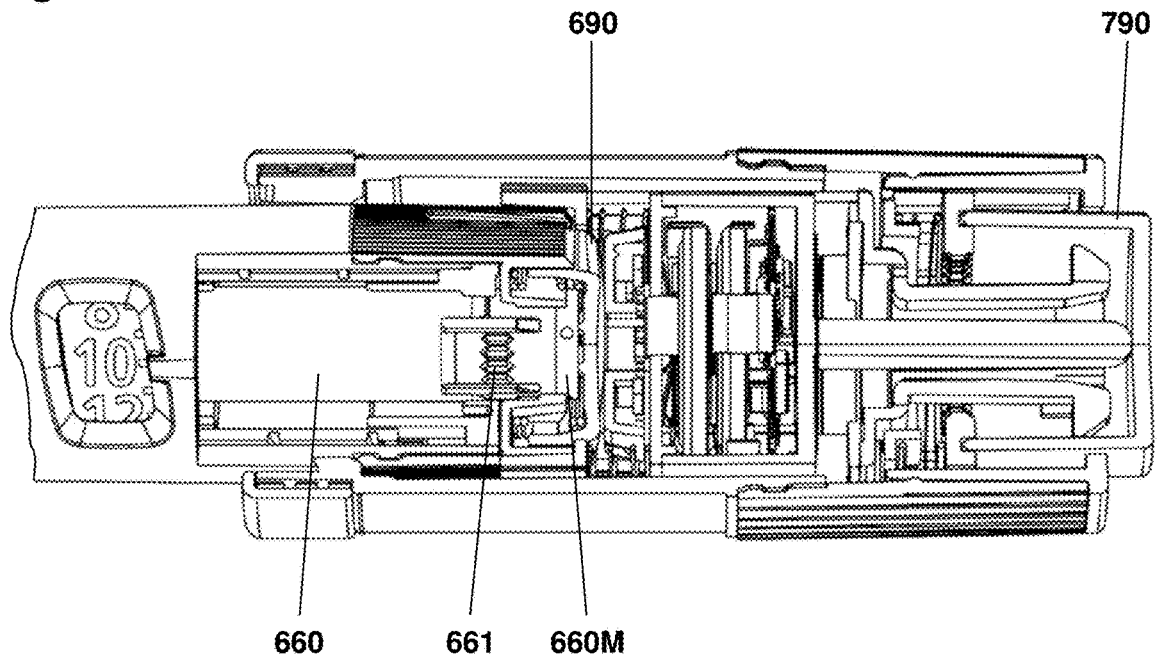
Figure 8D:
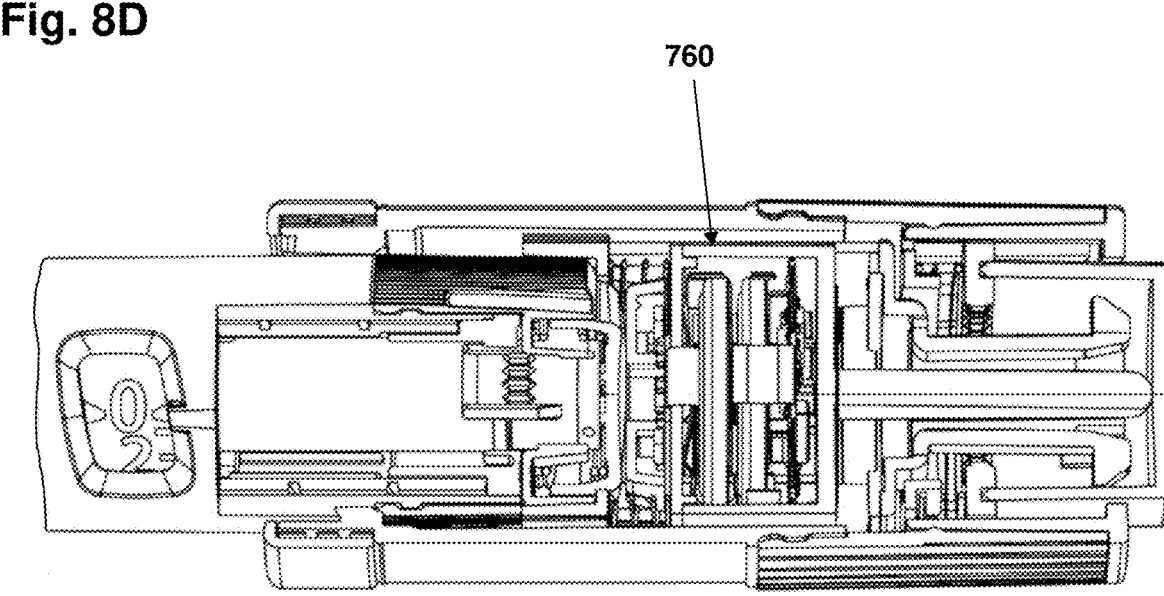
Figure 16:
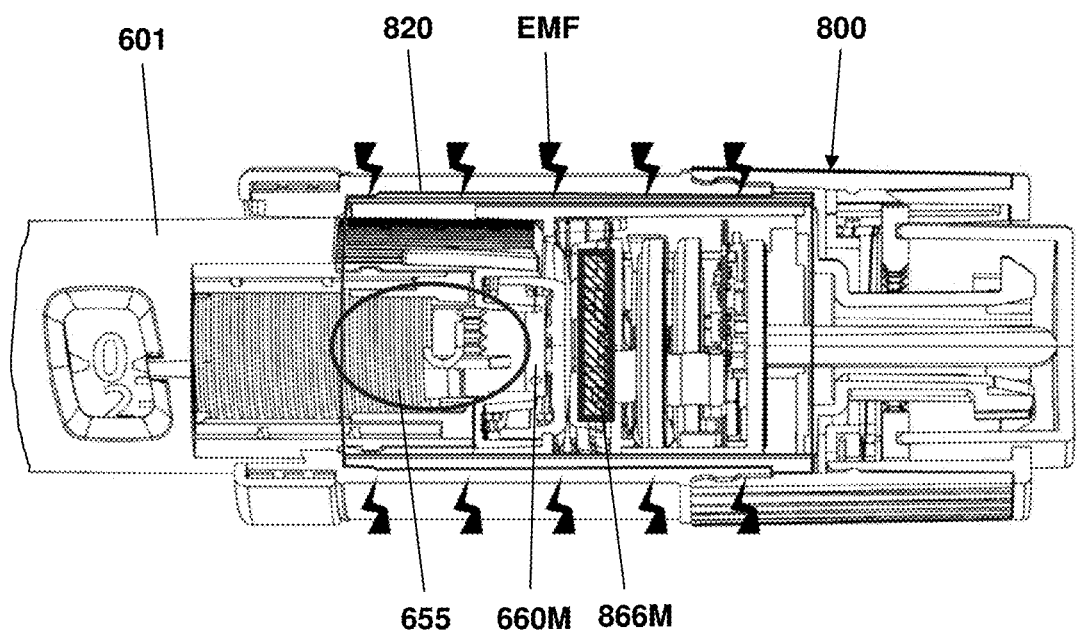
FIG. 16 shows a further embodiment of add-on device mounted on a drug delivery device.

FIG. 16 shows an assembly essentially corresponding to the assembly shown in FIG. 8A albeit with the drug delivery device torque spring 655 shown, the add-on dose logging device 800 being provided with a cylindrical shield 820 made of mu-metal covering the axial length of the sensors and tracer magnet volume, as well as the proximal part of the torque spring 655. The cylindrical mu-metal shield essentially absorbs the magnetic lines from a torque spring having been magnetized and guides them towards the circumferential shield and thereby limits the extent of the disturbing field of the torque spring in axial direction and thus towards the sensors. At the same time the cylindrical shield helps reduce the influence of external magnetic fields EMF on the sensor electronics arranged in the interior of the cylindrical volume.

Although the cylindrical mu-metal shield 820 principally will also absorb magnetic lines from the tracer magnet 660M, this will influence the measuring performance to a smaller degree as (i) the torque spring 655 is axially arranged farther away from the magnetic sensors 866M than the tracer magnet, and (ii) the torque spring is arranged radially closer to the shield than the tracer magnet. In this way the sensor system will be able to measure the magnetic field from the tracer magnet as only a smaller portion of the field is absorbed by the shield, whereas the above-described geometrical properties will allow a magnetic field from the torque spring to be absorbed by the shield to a high degree and thus influence the sensors to a smaller extent.

Figure 17:
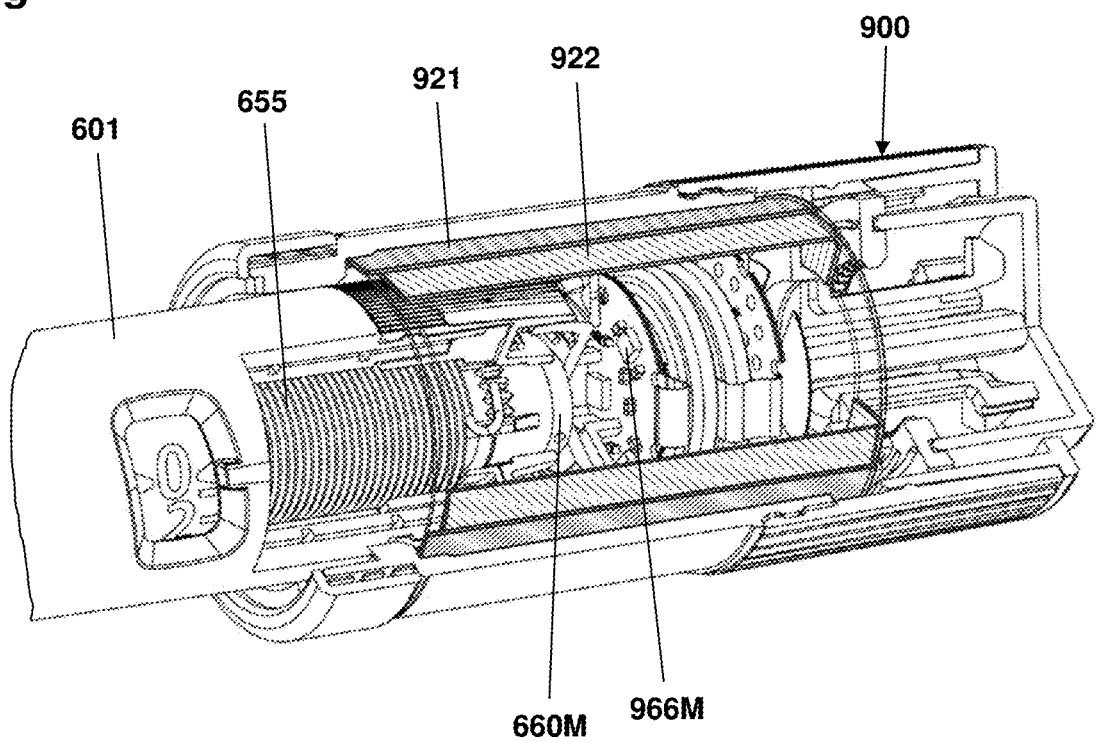
FIG. 17 shows a yet further embodiment of add-on device mounted on a drug delivery device.

FIG. 17 shows an embodiment of an add-on dose logging device 900 in which an outer shield of steel 921, able to handle stronger magnetic fields without saturation, is applied to provide a path for external magnetic fields. An inner shield 922 in mu-metal is arranged to provide a path for a relative weak internal magnetic field introduced by the torque spring, without being saturated by a strong external field.

In the above description of exemplary embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. A dose detection system comprising:
   a medication delivery device having a magnetic ring fixedly coupled to a dosing member and rotatable during dose setting and dose dispensing; and
   an electronics assembly comprising a processor and a plurality of magnetic sensors operably coupled to the processor,
   the magnetic sensors being arranged in an overlapping position relative to an outer circumference of the magnetic ring,
   wherein:
   the magnetic sensors are securely fixed relative to the processor,
   the magnetic sensors are rotatably locked to the magnetic ring during dose setting, thereby rotating therewith,
   the magnetic sensors are disposed equi-angularly relative to one another to define a ring pattern,
   in dose dispensing the magnetic sensors are distally moved closer to the magnetic ring, the magnetic ring rotating relative to the non-rotating magnetic sensors,
   the magnetic sensors detect rotational movement of the magnetic ring in order to generate position signals, and
   the processor is configured to receive the position signals in order to determine data indicative of an amount of dose dispensed based on the position signal.

2. The dose detection system as in claim 1, wherein the medication delivery device further comprises:
   drug expelling structure comprising a rotatable dose setting member allowing a user to set a dose amount of drug to be expelled,
   the electronics assembly being adapted to engage the dose setting member allowing a user to set a dose amount of drug to be expelled via the electronics assembly.

3. The dose detection system as in claim 1, wherein the magnetic sensors are arranged in a plane perpendicular to the rotational axis of the magnetic ring.

4. The dose detection system as in claim 1, wherein the magnetic sensors are arranged with circularly equal spacing.

5. The dose detection system as in claim 1, comprising 4, 5, 6, 7 or 8 magnetic sensors arranged in a circular pattern.

6. The dose detection system as in claim 1, wherein the magnetic sensors are arranged distally in the electronics assembly facing the magnetic ring in a mounted position.

7. The dose detection system as in claim 1, wherein the rotational position and/or a rotational movement of the magnetic ring is determined using a DFT algorithm.

8. An add-on device adapted to be releasably mounted on the proximal end of a drug delivery device, the drug delivery device comprising:
   a housing,
   an expelling mechanism adapted to expel a user-set amount of drug from a contained cartridge,
   an indicator element comprising a magnetic ring adapted to rotate relative to the housing during dose setting and/or expelling of a dose amount, the amount of movement being indicative of the size of the set and/or expelled dose amount, the indicator element comprising at least one dipole magnet,
   the add-on device comprising:
   a sensor system comprising:
   a plurality of magnetometers to determine magnetic field values from the at least one dipole magnet, and
   processor structure configured to determine, when the add-on device is mounted on the drug delivery device, on the basis of measured values from the plurality of magnetometers a rotational position and/or a rotational movement of an indicator element, the rotational position and/or a rotational movement of the indicator element corresponding to a set and/or expelled dose amount,
   wherein the magnetometers are arranged in a circular ring pattern.

9. The add-on device as in claim 8, wherein the drug delivery device further comprises:
   drug expelling structure comprising a rotatable dose setting member allowing a user to set a dose amount of drug to be expelled,
   the add-on device being adapted to engage the dose setting member allowing a user to set a dose amount of drug to be expelled via the add-on device.

10. The add-on device as in claim 8, wherein the magnetometers are arranged in a plane perpendicular to the rotational axis of the indicator element.

11. The add-on device as in claim 8, wherein the magnetometers are arranged with circularly equal spacing.

12. The add-on device as in claim 8, comprising 4, 5, 6, 7 or 8 magnetometers arranged in a circular pattern.

13. The add-on device as in claim 8, wherein the magnetometers are arranged distally in the add-on device facing the indicator element in a mounted position.

14. The add-on device as in claim 8, wherein the rotational position and/or a rotational movement of the indicator element is determined using a DFT algorithm.

* * * * *